United States Patent
DeVita et al.

(10) Patent No.: US 7,696,177 B2
(45) Date of Patent: Apr. 13, 2010

(54) ANTI-HYPERCHOLESTEROLEMIC COMPOUNDS

(75) Inventors: Robert J. DeVita, Westfield, NJ (US); Greg J. Morriello, Randolph, NJ (US); Anthony K. Ogawa, Mountainside, NJ (US); Feroze Ujjainwalla, Scotch Plains, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 281 days.

(21) Appl. No.: 11/922,055

(22) PCT Filed: Jun. 9, 2006

(86) PCT No.: PCT/US2006/022470
§ 371 (c)(1),
(2), (4) Date: Dec. 12, 2007

(87) PCT Pub. No.: WO2006/138163
PCT Pub. Date: Dec. 28, 2006

(65) Prior Publication Data
US 2010/0004184 A1    Jan. 7, 2010

Related U.S. Application Data

(60) Provisional application No. 60/690,856, filed on Jun. 15, 2005.

(51) Int. Cl.
A61K 31/67 (2006.01)
C07H 7/02 (2006.01)
A61K 31/70 (2006.01)
A61P 9/10 (2006.01)

(52) U.S. Cl. .................................. 514/23; 536/53
(58) Field of Classification Search .............. None
See application file for complete search history.

(56) References Cited

U.S. PATENT DOCUMENTS

| | | | |
|---|---|---|---|
| 5,756,470 A | 5/1998 | Yumibe et al. | |
| 5,846,966 A | 12/1998 | Rosenblum et al. | |
| RE37,721 E | 5/2002 | Rosenblum et al. | |
| 6,992,067 B2 * | 1/2006 | Glombik et al. | 514/23 |
| 7,045,515 B2 | 5/2006 | Tomiyama et al. | |
| 2002/0137689 A1 | 9/2002 | Glombik et al. | |
| 2005/0267049 A1 * | 12/2005 | Goulet et al. | 514/25 |

FOREIGN PATENT DOCUMENTS

WO    WO 2005/062824 A2    7/2005

OTHER PUBLICATIONS

Burnett et al., Bioorganic & Medicinal Chemistry Letters, vol. 12, pp. 311-314 (2002).

* cited by examiner

*Primary Examiner*—Shaojia Anna Jiang
*Assistant Examiner*—Bahar Schmidtmann
(74) *Attorney, Agent, or Firm*—Dianne Pecoraro; Mark R. Daniel; Carol S. Quagliato

(57) ABSTRACT

This invention provides cholesterol absorption inhibitors of Formula (I), and the pharmaceutically acceptable salts and esters thereof. The compounds are useful for lowering plasma cholesterol levels, particularly LDL cholesterol, and for treating and preventing atherosclerosis and atherosclerotic disease events.

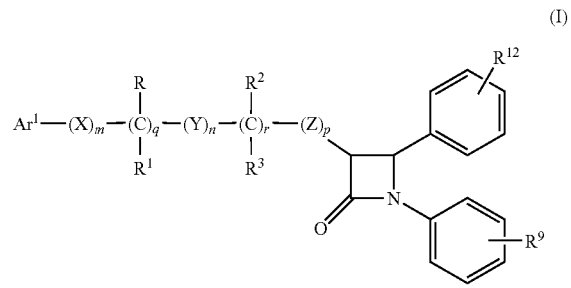

19 Claims, No Drawings

ANTI-HYPERCHOLESTEROLEMIC COMPOUNDS

PRIORITY CLAIM

This application is a §371 National Stage Application of PCT/US2006/022470, filed on Jun. 9, 2006, which claims priority from U.S. Provisional Application Ser. No. 60/690,856, filed on Jun. 15, 2005.

BACKGROUND OF THE INVENTION

The instant invention relates to substituted 2-azetidinones and the pharmaceutically acceptable salts and esters thereof, and to their use alone or in combination with other active agents to treat hypercholesterolemia and for preventing, halting or slowing the progression of atherosclerosis and related conditions and disease events.

It has been clear for several decades that elevated blood cholesterol is a major risk factor for coronary heart disease, and many studies have shown that the risk of CHD events can be reduced by lipid-lowering therapy. Prior to 1987, the lipid-lowering armamentarium was limited essentially to a low saturated fat and cholesterol diet, the bile acid sequestrants (cholestyramine and colestipol), nicotinic acid (niacin), the fibrates and probucol. Unfortunately, all of these treatments have limited efficacy or tolerability, or both. Substantial reductions in LDL (low density lipoprotein) cholesterol accompanied by increases in HDL (high density lipoprotein) cholesterol could be achieved by the combination of a lipid-lowering diet and a bile acid sequestrant, with or without the addition of nicotinic acid. However, this therapy is not easy to administer or tolerate and was therefore often unsuccessful except in specialist lipid clinics. The fibrates produce a moderate reduction in LDL cholesterol accompanied by increased HDL cholesterol and a substantial reduction in triglycerides, and because they are well tolerated these drugs have been more widely used. Probucol produces only a small reduction in LDL cholesterol and also reduces HDL cholesterol, which, because of the strong inverse relationship between HDL cholesterol level and CHD risk, is generally considered undesirable. With the introduction of lovastatin, the first inhibitor of HMG-CoA reductase to become available for prescription in 1987, for the first time physicians were able to obtain large reductions in plasma cholesterol with very few adverse effects.

Recent studies have unequivocally demonstrated that lovastatin, simvastatin and pravastatin, all members of the HMG-CoA reductase inhibitor class, slow the progression of atherosclerotic lesions in the coronary and carotid arteries. Simvastatin and pravastatin have also been shown to reduce the risk of coronary heart disease events, and in the case of simvastatin a highly significant reduction in the risk of coronary death and total mortality has been shown by the Scandinavian Simvastatin Survival Study. This study also provided some evidence for a reduction in cerebrovascular events. Despite the substantial reduction in the risk of coronary morbidity and mortality achieved by simvastatin, the risk is still substantial in the treated patients. For example, in the Scandinavian Simvastatin Survival Study, the 42% reduction in the risk of coronary death still left 5% of the treated patients to die of their disease over the course of this 5 year study. Further reduction of risk is clearly needed.

A more recent class of anti-hyperlipidemic agents that has emerged includes inhibitors of cholesterol absorption. Ezetimibe, the first compound to receive regulatory approval in this class, is currently marketed in the U.S. under the tradename ZETIA®. Ezetimibe has the following chemical structure and is described in U.S. Pat. No. Re. 37721 and U.S. Pat. No. 5,846,966:

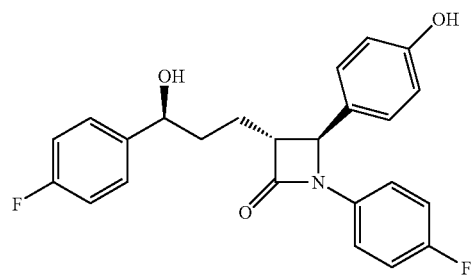

Sugar-substituted 2-azetidinones, including glucuronidated analogs of the following general structure:

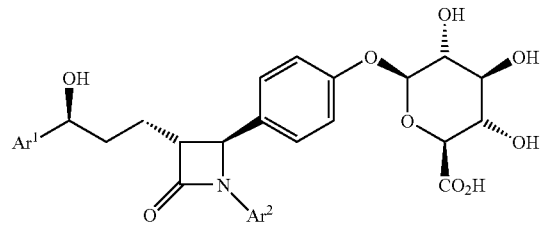

and methods for making them are disclosed in U.S. Pat. No. 5,756,470, wherein $Ar^1$ and $Ar^2$ are unsubstituted or substituted aryl groups.

Additional cholesterol absorption inhibitors are described in WO2002/066464 A1 (applied for by Kotobuki Pharmaceutical Co.), and US2002/0137689 A1 (Glombik et al.). WO2002/066464 A1 discloses hypolipidemic compounds of general formula

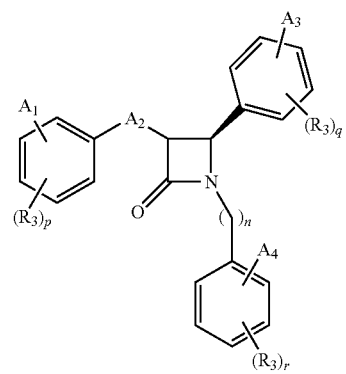

wherein, among other definitions, $A_1$, $A_3$ and $A_4$ can be

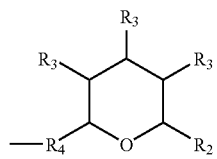

and wherein $R_2$ is —$CH_2OH$, —$CH_2OC(O)$—$R_1$, or —$CO_2R_1$; $R_3$ is —OH or —$OC(O)R_1$, and $R_4$ is —$(CH_2)_kR_5$ $(CH_2)_i$— where k and i are zero or integers of one or more, and k+i is an integer of 10 or less; and $R_5$ is a single bond, —CH=CH—, —$OCH_2$—, carbonyl or —CH(OH).

US2002/0137689 A1 discloses hypolipidemic compounds of general formula

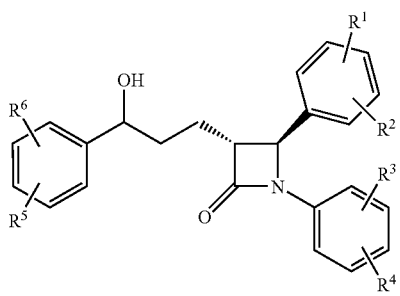

wherein, among other definitions, $R^1$, $R^2$, $R^3$, $R^4$, $R^5$, $R^6$ independently of one another can be $(C_0-C_{30})$-alkylene-(LAG), where one or more carbon atoms of the alkylene radical may be replaced by —O—, —(C=O)—, —CH=CH—, —C≡C—, —$N((C_1-C_6)$-alkyl)-, —$N((C_1-C_6)$-alkylphenyl) or —NH—; and (LAG) is a sugar residue, disugar residue, trisugar residue, tetrasugar residue; a sugar acid, or an amino sugar.

In the ongoing effort to discover novel treatments for hyperlipidemia and atherosclerotic process, the instant invention provides novel cholesterol absorption inhibitors, described below.

SUMMARY OF THE INVENTION

One object of the instant invention provides novel cholesterol absorption inhibitors of Formula I

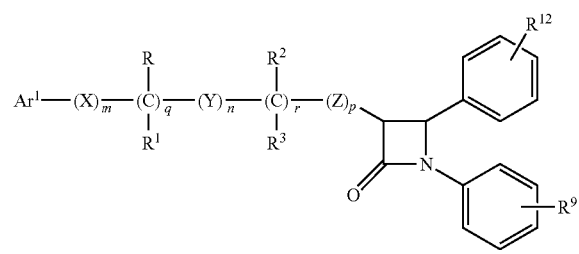

and the pharmaceutically acceptable salts and esters thereof.

A second object of the instant invention is to provide a method for inhibiting cholesterol absorption comprising administering a therapeutically effective amount of a compound of Formula I to a patient in need of such treatment. Another object is to provide a method for reducing plasma cholesterol levels, especially LDL-cholesterol, and treating hypercholesterolemia comprising administering a therapeutically effective amount of a compound of Formula I to a patient in need of such treatment.

As a further object, methods are provided for preventing or reducing the risk of developing atherosclerosis, as well as for halting or slowing the progression of atherosclerotic disease once it has become clinically evident, comprising the administration of a prophylactically or therapeutically effective amount, as appropriate, of a compound of Formula I to a patient who is at risk of developing atherosclerosis or who already has atherosclerotic disease. Another object of the present invention is the use of the compounds of the present invention for the manufacture of a medicament useful in treating, preventing or reducing the risk of developing these conditions. Other objects of this invention are to provide processes for making the compounds of Formula I and to provide novel pharmaceutical compositions comprising these compounds.

Additionally the compounds of this invention, particularly radioactive isotopes of the compounds of Formula I, can be used in screening assays, where the assay is designed to identify new cholesterol absorption inhibitors that have the same mechanism of action as ezetimibe. Additional objects will be evident from the following detailed description.

DETAILED DESCRIPTION OF THE INVENTION

The novel cholesterol absorption inhibitors of the instant invention are compounds of the structural Formula I

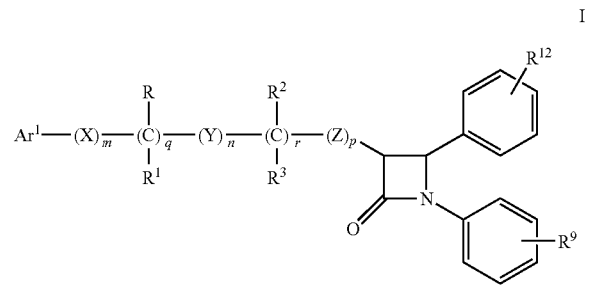

and the pharmaceutically acceptable salts and esters thereof, wherein $Ar^1$ is selected from the group consisting of aryl and $R^4$-substituted aryl;

X, Y and Z are independently selected from the group consisting of —$CH_2$—, —$CH(C_{1-6}alkyl)$— and —$C(C_{1-6}alkyl)_2$—;

R is selected from the group consisting of —$OR^6$, —$O(CO)R^6$, —$O(CO)OR^8$, —$O(CO)NR^6R^7$, a sugar residue, a disugar residue, a trisugar residue and a tetrasugar residue;

$R^1$ is selected from the group consisting of —H, —$C_{1-6}$alkyl and aryl, or R and $R^1$ together are oxo;

$R^2$ is selected from the group consisting of —$OR^6$, —$O(CO)R^6$, —$O(CO)OR^8$ and —$O(CO)NR^6R^7$;

$R^3$ is selected from the group consisting of —H, —$C_{1-6}$alkyl and aryl, or $R^2$ and $R^3$ together are oxo;

q and r are integers each independently selected from 0 and 1 provided that at least one of q and r is 1;

m, n and p are integers each independently selected from 0, 1, 2, 3 and 4, provided that the sum of m, n, p, q and r is 1, 2, 3, 4, 5 or 6;

t is an integer selected from 0, 1 and 2;

$R^4$ is 1-5 substituents independently selected at each occurrence from the group consisting of:
—$OR^5$, —$O(CO)R^5$, —$O(CO)OR^8$, —O—$C_{1-5}$alkyl-$OR^5$, —$O(CO)NR^5R^6$, —$NR^5R^6$, —$NR^5(CO)R^6$, —$NR^5(CO)OR^8$, —$NR^5(CO)NR^6R^7$, —$NR^5SO_2R^8$, —$COOR^5$, —$CONR^5R^6$, —$COR^5$, —$SO_2NR^5R^6$, —$S(O)_tR^8$, —O—$C_{1-10}$alkyl-$COOR^5$, —O—$C_{1-10}$alkyl-$CONR^5R^6$ and fluoro;

$R^5$, $R^6$ and $R^7$ are independently selected at each occurrence from the group consisting of —H, —$C_{1-6}$alkyl, aryl and aryl-substituted —$C_{1-6}$alkyl;

$R^8$ is independently selected from the group consisting of —$C_{1-6}$alkyl, aryl and aryl-substituted —$C_{1-6}$alkyl;

$R^9$ is selected from the group consisting of —C≡C—$(CH_2)_y$—$NR^{10}R^{11}$, —$(CH_2)_2$—$(CH_2)_y NR^{10}R^{11}$ and —C≡C—$C(O)R^{16}$;

$R^{10}$ is independently selected at each occurrence from —H and —$C_{1-3}$alkyl;

$R^{11}$ is selected from the group consisting of —H, —$C_{1-3}$alkyl, —C(O)—$C_{1-3}$alkyl, —C(O)—$NR^{10}R^{10}$, —$SO_2$—$C_{1-3}$alkyl, and —$SO_2$-phenyl; and $R^{12}$ is selected from the group consisting of $R^{13}$, —$C_{1-8}$alkyl-$R^{13}$, —CH=CH—$(CH_2)_w$—$R^{13}$ and —C≡C—$(CH_2)_w$—$R^{13}$, provided that when $R^{12}$ is —$C_{1-8}$alkyl-$R^{13}$ then $R^9$ is —$(CH_2)_2$—$(CH_2)_y NR^{10}R^{11}$;

w is an integer independently selected at each occurrence from 0, 1, 2, 3, 4, 5 and 6;

y is an integer independently selected at each occurrence from 1, 2, 3, 4, 5 and 6;

$R^{13}$ is

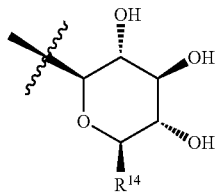

$R^{14}$ is selected from the group consisting of —COOH, —$COOC_{1-6}$-alkyl, —$CH_2OH$, —$CH_2O(CH_2)_y$—$R^{15}$,

$R^{15}$ is independently selected at each occurrence from the group consisting of —H, —OH, —$COOR^{10}$, —$NR^{10}R^{17}$, —$NR^{10}COR^{17}$, —$NR^{10}COOR^{17}$, —$NR^{10}$—$SO_2R^{17}$ and —$NR^{10}$—$CONR^{10}R^{17}$;

$R^{16}$ is selected from the group consisting of —OH, —$OC_{1-6}$alkyl and —$NR^{10}R^{11}$; and $R^{17}$ is selected from the group consisting of —H, —$C_{1-3}$alkyl, phenyl and —$CH_2$-phenyl.

In one embodiment of this invention are compounds defined above for Formula I provided that when p is 0 and r is 1, the sum of m, q and n is 1, 2, 3, 4, or 5.

In a second embodiment of this invention are compounds Formula I having structural Formula Ia,

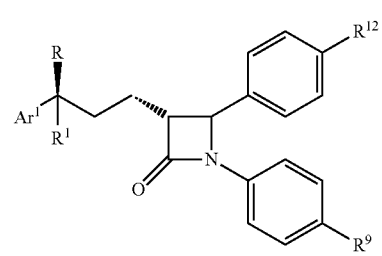

and the pharmaceutically acceptable salts and esters thereof, wherein the variables are as defined in Formula I.

In a third embodiment of this invention are compounds Formula I having structural Formula Ib,

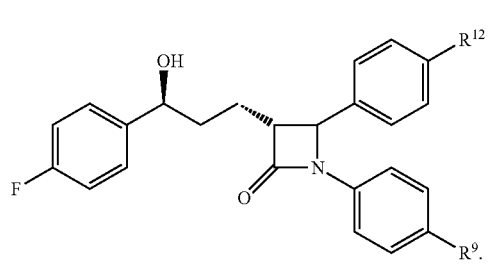

and the pharmaceutically acceptable salts and esters thereof, wherein the variables are as defined in Formula I.

In another embodiment of this invention are compounds of Formula I wherein m is 0, q is 1, n is 1, r is 0 and p is 1. In a class of this embodiment, Y and Z are —$CH_2$—. In a subclass of this embodiment, R is —OH and $R^1$ is —H.

In another embodiment of this invention are compounds of Formulas I and Ia wherein $Ar^1$ is as defined above in Formula I. In a class of this embodiment, $Ar^1$ is selected from the group consisting of aryl and $R^4$-substituted aryl wherein $R^4$ is 1-2 substituents independently selected at each occurrence from the group consisting of: —$OR^5$, —$O(CO)R^5$, —$O(CO)OR^8$, —O—$C_{1-5}$alkyl-$OR^5$, —$O(CO)NR^5R^6$, —$NR^5R^6$, —$NR^5(CO)R^6$, —$NR^5(CO)OR^8$, —$NR^5(CO)NR^6R^7$, —$NR^5SO_2R^8$, —$COOR^5$, —$CONR^5R^6$, —$COR^5$, —$SO_2NR^5R^6$, —$S(O)_tR^8$, —O—$C_{1-10}$alkyl-$COOR^5$, —O—$C_{1-10}$alkyl-$CONR^5R^6$ and fluoro. In a subclass of this embodiment, $Ar^1$ is unsubstituted, mono- or di-substituted phenyl. In a further sub-class, $Ar^1$ is phenyl mono-substituted with fluoro, and particularly 4-fluoro-phenyl.

In another embodiment of this invention are compounds of Formulas I and Ia wherein R is as defined above in Formula I. In a class of this embodiment, R is —$OR^6$; in a subclass of this embodiment, R is —OH.

In another embodiment of this invention are compounds of Formulas I and Ia wherein $R^1$ is as defined above in Formula I. In a class of this embodiment, $R^1$ is —H.

In another embodiment of this invention are compounds of Formula I, Ia and Ib wherein $R^9$ is as defined above in Formula I. In a class of this embodiment, $R^9$ is selected from —C≡C—$(CH_2)_y$—$NR^{10}R^{11}$ and —$(CH_2)_2$—$(CH_2)_y$ $NR^{10}R^{11}$, and in a sub-class $R^9$ is selected from —C≡C—$CH_2$—$NR^{10}R^{11}$ and —$(CH_2)_3$—$NR^{10}R^{11}$. In a further sub-class of this embodiment, $R^9$ is selected from —C≡C—$CH_2$—$N(R^{10})(SO_2$—$C_{1-3}$alkyl), —C≡C—$CH_2$—$N(R^{10})$ ($SO_2$-phenyl), —$(CH_2)_3$—$N(R^{10})(SO_2$—$C_{1-3}$alkyl) and —$(CH_2)_3$—$N(R^{10})(SO_2$-phenyl).

In another embodiment of this invention are compounds of Formula I, Ia and Ib wherein $R^{12}$ is as defined above in Formula I. In a class of this embodiment, $R^{12}$ is selected from $R^{13}$, —$CH_2$—$R^{13}$, —$CH_2$—$CH_2$—$R^{13}$ and —C≡C—$R^{13}$.

Each embodiment, class or sub-class described above for each variable (i.e., $Ar^1$, R, $R^1$, $R^9$, $R^{12}$) in Formulas I, Ia, Ib, may be combined with one or more of the embodiments, classes or sub-classes described above for one or more other variables, and all such sub-generic combinations are included within the scope of this invention.

As used herein "alkyl" is intended to include both branched- and straight-chain saturated aliphatic hydrocarbon groups having the specified number of carbon atoms. Examples of alkyl groups include, but are not limited to, methyl (Me), ethyl (Et), n-propyl (Pr), n-butyl (Bu), n-pentyl, n-hexyl, and the isomers thereof such as isopropyl (i-Pr), isobutyl (i-Bu), secbutyl (s-Bu), tertbutyl (t-Bu), isopentyl, isohexyl and the like. If there is no specified prefix (such as "n-" for normal, "s-" for sec, "t-" for tert, "i-" for iso) with a named alkyl group, then it is intended that the named alkyl group is an n-alkyl group (i.e., "propyl" is "n-propyl"). As used herein within the definitions of variable groups in Formula I, "alkyl" may be univalent, as for example when $R^8$ is —$C_{1-6}$alkyl, or it may be divalent, as for example when $R^8$ is aryl-substituted —$C_{1-6}$alkyl or when $R^{12}$ is —$C_{1-6}$alkyl-$R^{13}$.

As used herein, "aryl" is intended to include phenyl (Ph), naphthyl, indenyl, tetrahydronaphthyl or indanyl. Phenyl is preferred.

Hydroxyl protecting groups may be used on intermediates during the synthetic procedures for making final products within the scope of this invention. Suitable protecting groups (designated as "PG" herein) for the hydroxyl groups of $R^{13}$ include but are not limited to those that are known to be useful as carbohydrate protecting groups, such as for example benzyl, acetyl, benzoyl, tert-butyldiphenylsilyl, trimethylsilyl, para-methoxybenzyl, benzylidine, and methoxy methyl. Conditions required to selectively add and remove such protecting groups are found in standard textbooks such as Greene, T, and Wuts, P. G. M., *Protective Groups in Organic Synthesis*, John Wiley & Sons, Inc., New York, N.Y., 1999.

Compounds of Formula I may contain one or more asymmetric centers and can thus occur as racemates and racemic mixtures, single enantiomers, enantiomeric mixtures, diastereomeric mixtures and individual diastereomers. The present invention is meant to comprehend all such isomeric forms of the compounds of Formula I. All such isomeric forms of the compounds of Formula I are included within the scope of this invention. Furthermore, some of the crystalline forms for compounds of the present invention may exist as polymorphs and as such are intended to be included in the present invention. In addition, some of the compounds of the instant invention may form solvates with water or organic solvents. Such hydrates and solvates are also encompassed within the scope of this invention.

Due to their activity as cholesterol absorption inhibitors, the compounds of the present invention can be used in screening assays, where the assay is designed to identify new cholesterol absorption inhibitors. Radioactive isotopes of the compounds of Formula I are particularly useful in such assays, for example compounds of Formula I wherein sulfur is replaced with "hot" —$^{35}S$—, and particularly wherein the radioactive sulfur isotope is incorporated within the $R^9$ moiety. All such radioactive isotopes of the compounds of Formula I are included within the scope of this invention.

Herein, the term "pharmaceutically acceptable salts" shall mean non-toxic salts of the compounds employed in this invention which are generally prepared by reacting the free acid with a suitable organic or inorganic base, particularly those formed from cations such as sodium, potassium, aluminum, calcium, lithium, magnesium, zinc and tetramethylammonium, as well as those salts formed from amines such as ammonia, ethylenediamine, N-methylglucamine, lysine, arginine, ornithine, choline, N,N'-dibenzylethylenediamine, chloroprocaine, diethanolamine, procaine, N-benzylphenethylamine, 1-p-chlorobenzyl-2-pyrrolidine-1'-yl-methylbenzimidazole, diethylamine, piperazine, morpholine, 2,4,4-trimethyl-2-pentamine and tris(hydroxymethyl)aminomethane.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

Examples of pharmaceutically acceptable esters include, but are not limited to, —$C_{1-4}$alkyl and —$C_{1-4}$alkyl substituted with phenyl, dimethylamino and acetylamino. "$C_{1-4}$alkyl" herein includes straight or branched aliphatic chains containing from 1 to 4 carbon atoms, for example methyl, ethyl, n-propyl, n-butyl, iso-propyl, sec-butyl and tert-butyl.

The term "patient" includes mammals, especially humans, who use the instant active agents for the prevention or treatment of a medical condition. Administering of the drug to the patient includes both self-administration and administration to the patient by another person. The patient may be in need of treatment for an existing disease or medical condition, or may desire prophylactic treatment to prevent or reduce the risk for diseases and medical conditions affected by inhibition of cholesterol absorption.

The term "therapeutically effective amount" is intended to mean that amount of a drug or pharmaceutical agent that will elicit the biological or medical response of a tissue, a system, animal or human that is being sought by a researcher, veterinarian, medical doctor or other clinician. The term "prophylactically effective amount" is intended to mean that amount of a pharmaceutical drug that will prevent or reduce the risk of occurrence of the biological or medical event that is sought to be prevented in a tissue, a system, animal or human by a researcher, veterinarian, medical doctor or other clinician. Particularly, the dosage a patient receives can be selected so as to achieve the amount of LDL cholesterol lowering desired; the dosage a patient receives may also be titrated over time in order to reach a target LDL level. The dosage regimen utilizing a compound of the instant invention is selected in accordance with a variety of factors including type, species, age, weight, sex and medical condition of the patient; the severity of the condition to be treated; the potency of the compound chosen to be administered; the route of administration; and the renal and hepatic function of the patient. A consideration of these factors is well within the purview of the ordinarily skilled clinician for the purpose of determining the therapeutically effective or prophylactically effective dosage amount needed to prevent, counter, or arrest the progress of the condition.

The compounds of the instant invention are cholesterol absorption inhibitors and are useful for reducing plasma cholesterol levels, particularly reducing plasma LDL cholesterol levels, when used either alone or in combination with another active agent, such as an anti-atherosclerotic agent, and more particularly a cholesterol biosynthesis inhibitor, for example an HMG-CoA reductase inhibitor. Thus the instant invention provides methods for inhibiting cholesterol absorption and for treating lipid disorders including hypercholesterolemia, comprising administering a therapeutically effective amount of a compound of Formula I to a person in need of such treatment. Further provided are methods for preventing or reducing the risk of developing atherosclerosis, as well as for halting or slowing the progression of atherosclerotic disease once it has become clinically evident, comprising the administration of a prophylactically or therapeutically effective amount, as appropriate, of a compound of Formula I to a mammal who is at risk of developing atherosclerosis or who already has atherosclerotic disease.

Atherosclerosis encompasses vascular diseases and conditions that are recognized and understood by physicians practicing in the relevant fields of medicine. Atherosclerotic cardiovascular disease including restenosis following revascularization procedures, coronary heart disease (also known as coronary artery disease or ischemic heart disease), cerebrovascular disease including multi-infarct dementia, and peripheral vessel disease including erectile dysfunction are all clinical manifestations of atherosclerosis and are therefore encompassed by the terms "atherosclerosis" and "atherosclerotic disease."

A compound of Formula I may be administered by prevent or reduce the risk of occurrence, or recurrence where the potential exists, of a coronary heart disease event, a cerebrovascular event, and/or intermittent claudication. Coronary heart disease events are intended to include CHD death, myocardial infarction (i.e., a heart attack), and coronary revascularization procedures. Cerebrovascular events are intended to include ischemic or hemorrhagic stroke (also known as cerebrovascular accidents) and transient ischemic attacks. Intermittent claudication is a clinical manifestation of peripheral vessel disease. The term "atherosclerotic disease event" as used herein is intended to encompass coronary heart disease events, cerebrovascular events, and intermittent claudication. It is intended that persons who have previously experienced one or more non-fatal atherosclerotic disease events are those for whom the potential for recurrence of such an event exists.

Accordingly, the instant invention also provides a method for preventing or reducing the risk of a first or subsequent occurrence of an atherosclerotic disease event comprising the administration of a prophylactically effective amount of a compound of Formula I to a patient at risk for such an event. The patient may or may not have atherosclerotic disease at the time of administration, or may be at risk for developing it.

Persons to be treated with the instant therapy include those at risk of developing atherosclerotic disease and of having an atherosclerotic disease event. Standard atherosclerotic disease risk factors are known to the average physician practicing in the relevant fields of medicine. Such known risk factors include but are not limited to hypertension, smoking, diabetes, low levels of high density lipoprotein (HDL) cholesterol, and a family history of atherosclerotic cardiovascular disease. Published guidelines for determining those who are at risk of developing atherosclerotic disease can be found in: Executive Summary of the Third Report of the National Cholesterol Education Program (NCEP) Expert Panel on Detection, Evaluation, and Treatment of High Blood Cholesterol in Adults (Adult Treatment Panel III), JAMA, 2001; 285 pp. 2486-2497. People who are identified as having one or more of the above-noted risk factors are intended to be included in the group of people considered at risk for developing atherosclerotic disease. People identified as having one or more of the above-noted risk factors, as well as people who already have atherosclerosis, are intended to be included within the group of people considered to be at risk for having an atherosclerotic disease event.

The oral dosage amount of the compound of Formula I, is from about 0.1 to about 30 mg/kg of body weight per day, preferably about 0.1 to about 15 mg/kg of body weight per day. For an average body weight of 70 kg, the dosage level is therefore from about 5 mg to about 1000 mg of drug per day. However, dosage amounts will vary depending on factors as noted above, including the potency of the particular compound. Although the active drug of the present invention may be administered in divided doses, for example from two to four times daily, a single daily dose of the active drug is preferred. As examples, the daily dosage amount may be selected from, but not limited to, 5 mg, 10 mg, 15 mg, 20 mg, 25 mg, 40 mg, 50 mg, 75 mg, 80 mg, 100 mg and 200 mg.

The active drug employed in the instant therapy can be administered in such oral forms as tablets, capsules, pills, powders, granules, elixirs, tinctures, suspensions, syrups, and emulsions. Oral formulations are preferred.

For compounds of Formula I, administration of the active drug can be via any pharmaceutically acceptable route and in any pharmaceutically acceptable dosage form. This includes the use of oral conventional rapid-release, time controlled-release and delayed-release (such enteric coated) pharmaceutical dosage forms. Additional suitable pharmaceutical compositions for use with the present invention are known to those of ordinary skill in the pharmaceutical arts; for example, see Remington's Pharmaceutical Sciences, Mack Publishing Co., Easton, Pa.

In the methods of the present invention, the active drug is typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with a non-toxic, pharmaceutically acceptable, inert carrier such as lactose, starch, sucrose, glucose, modified sugars, modified starches, methyl cellulose and its derivatives, dicalcium phosphate, calcium sulfate, mannitol, sorbitol and other reducing and non-reducing sugars, magnesium stearate, steric acid, sodium stearyl fumarate, glyceryl behenate, calcium stearate and the like. For oral administration in liquid form, the drug components can be combined with non-toxic, pharmaceutically acceptable inert carrier such as ethanol, glycerol, water and the like. Moreover, when desired or necessary, suitable binders, lubricants, disintegrating agents and coloring and flavoring agents can also be incorporated into the mixture. Stabilizing agents such as antioxidants, for example butylated hydroxyanisole (BHA), 2,6-di-tert-butyl-4-methylphenol (BHT), propyl gallate, sodium ascorbate, citric acid, calcium metabisulphite, hydroquinone, and 7-hydroxycoumarin, particularly BHA, propyl gallate and combinations thereof, can also be added to stabilize the dosage forms. When a compound of Formula I is formulated together with an HMG-CoA reductase inhibitor such as simvastatin, the use of at least one stabilizing agent is preferred in the composition. Other suitable components include gelatin, sweeteners, natural and synthetic gums such as acacia, tragacanth or alginates, carboxymethylcellulose, polyethylene glycol, waxes and the like.

The active drug can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Active drug may also be delivered by the use of monoclonal antibodies as individual carriers to which the compound molecules are coupled. Active drug may also be coupled with soluble polymers as targetable drug carriers. Such polymers can include polyvinyl-pyrrolidone, pyran copolymer, polyhydroxy-propyl-metheacrylamide-phenol, polyhydroxy-ethyl-aspartamide-phenol, or polyethyleneoxide-polylysine substituted with palmitoyl residues. Furthermore, active drug may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The instant invention also encompasses a process for preparing a pharmaceutical composition comprising combining a compound of Formula I with a pharmaceutically acceptable carrier. Also encompassed is the pharmaceutical composition which is made by combining a compound of Formula I with a pharmaceutically acceptable carrier.

One or more additional active agents may be administered in combination with a compound of Formula I, and therefore an embodiment of the instant invention encompasses a drug combination. The drug combination encompasses a single dosage formulation comprised of the compound of Formula I and additional active agent or agents, as well as administration of each of the compound of Formula I and the additional active agent or agents in separate dosage formulations, which allows for concurrent or sequential administration of the active agents. The additional active agent or agents can be lipid modifying agents, particularly a cholesterol biosynthesis inhibitor such as an HMG-CoA reductase inhibitor, or agents having other pharmaceutical activities, or agents that have both lipid-modifying effects and other pharmaceutical activities. Examples of HMG-CoA reductase inhibitors useful for this purpose include statins in their lactonized or dihydroxy open acid forms and pharmaceutically acceptable salts and esters thereof, including but not limited to lovastatin (MEVACOR®; see U.S. Pat. No. 4,342,767); simvastatin (ZOCOR®; see U.S. Pat. No. 4,444,784); dihydroxy open-acid simvastatin, particularly the ammonium or calcium salts thereof; pravastatin, particularly the sodium salt thereof (PRAVACOL®; see U.S. Pat. No. 4,346,227); fluvastatin particularly the sodium salt thereof (LESCOL®; see U.S. Pat. No. 5,354,772); atorvastatin, particularly the calcium salt thereof (LIPITOR®; see U.S. Pat. No. 5,273,995); rosuvastatin (CRESTOR®; see U.S. Pat. No. 5,260,440); and pitavastatin also referred to as NK-104 (see PCT international publication number WO 97/23200). Examples of additional active agents which may be employed include but are not limited to one or more of FLAP inhibitors; 5-lipoxygenase inhibitors; additional cholesterol absorption inhibitors such as ezetimibe (ZETIA®), described in U.S. Pat. No. Re. 37721 and U.S. Pat. No. 5,846,966; cholesterol ester transfer protein (CETP) inhibitors, for example JTT-705 and torcetrapib, also known as CP529,414; HMG-CoA synthase inhibitors; squalene epoxidase inhibitors; squalene synthetase inhibitors (also known as squalene synthase inhibitors); acyl-coenzyme A: cholesterol acyltransferase (ACAT) inhibitors including selective inhibitors of ACAT-1 or ACAT-2 as well as dual inhibitors of ACAT1 and -2; microsomal triglyceride transfer protein (MTP) inhibitors; niacin; bile acid sequestrants; LDL (low density lipoprotein) receptor inducers; platelet aggregation inhibitors, for example glycoprotein IIb/IIIa fibrinogen receptor antagonists and aspirin; human peroxisome proliferator activated receptor gamma (PPARγ) agonists including the compounds commonly referred to as glitazones for example pioglitazone and rosiglitazone and, including those compounds included within the structural class known as thiazolidinediones as well as those PPARγ agonists outside the thiazolidinedione structural class; PPARα agonists such as clofibrate, fenofibrate including micronized fenofibrate, and gemfibrozil; PPAR dual α/γ agonists; vitamin $B_6$ (also known as pyridoxine) and the pharmaceutically acceptable salts thereof such as the HCl salt; vitamin $B_{12}$ (also known as cyanocobalamin); folic acid or a pharmaceutically acceptable salt or ester thereof such as the sodium salt and the methylglucamine salt; anti-oxidant vitamins such as vitamin C and E and beta carotene; beta-blockers; angiotensin II antagonists such as losartan; angiotensin converting enzyme inhibitors such as enalapril and captopril; calcium channel blockers such as nifedipine and diltiazam; endothelian antagonists; agents that enhance ABC1 gene expression; FXR ligands including both inhibitors and agonists; and LXR ligands including both inhibitors and agonists of all sub-types of this receptor, e.g. LXRα and LXRβ; bisphosphonate compounds such as alendronate sodium; and cyclooxygenase-2 inhibitors such as rofecoxib, celecoxib and valdecoxib.

A therapeutically or prophylactically effective amount, as appropriate, of a compound of Formula I can be used for the preparation of a medicament useful for inhibiting cholesterol absorption, as well as for treating and/or reducing the risk for diseases and conditions affected by inhibition of cholesterol absorption, such as treating lipid disorders, preventing or reducing the risk of developing atherosclerotic disease, halting or slowing the progression of atherosclerotic disease once it has become clinically manifest, and preventing or reducing the risk of a first or subsequent occurrence of an atherosclerotic disease event. For example, the medicament may be comprised of about 5 mg to about 1000 mg of a compound of Formula I. The medicament comprised of a compound of Formula I may also be prepared with one or more additional active agents, such as those described supra.

Compounds of this invention were determined to inhibit cholesterol absorption employing the Cholesterol Absorption Assay in Mice, below. This assay involves comparing a test compound to ezetimibe with respect to their ability to inhibit cholesterol absorption in mice. Both ezetimibe and the tested compounds of this invention inhibited cholesterol absorption by >90% at the highest dose tested. The tested compounds had an ID 50<1 mg/kg.

Cholesterol Absorption Assay in Mice:

C57BL/6 male mice (n=6/group), aged 10-14 weeks, were dosed orally with 0.2 ml 0.25% methyl cellulose solution with or without test compound or ezetimibe (0.12-10 mg/kg). Thirty minutes later all of the mice were dosed orally with 0.2 ml INTRALIPID™ containing 2 µCi [$^3$H]-cholesterol per mouse. Five hours later, the animals were euthanized, and liver and blood were collected. Cholesterol counts in liver and plasma were determined, and percent inhibition of cholesterol absorption was calculated.

The compounds of structural Formula I of the present invention can be prepared according to the procedures of the following Scheme and Examples, using appropriate materials, and are further exemplified by specific examples which follow. Moreover, by utilizing the procedures described herein, one of ordinary skill in the art can readily prepare additional compounds of the present invention claimed herein. The compounds illustrated in the examples are not, however, to be construed as forming the only genus that is considered as the invention. The Examples further illustrate details for the preparation of the compounds of the present invention. Those skilled in the art will readily understand that known variations of the conditions and processes of the following preparative procedures can be used to prepare these compounds.

A variety of chromatographic techniques may be employed in the preparation of the compounds. These techniques include, but are not limited to: High Performance Liquid Chromatography (including normal- reversed- and chiral-phase); Super Critical Fluid Chromatography; preparative Thin Layer Chromatography; flash chromatography with silica gel or reversed-phase silica gel; ion-exchange chromatography; and radical chromatography. All temperatures are degrees Celsius unless otherwise noted.

Some abbreviations used herein include:

| | |
|---|---|
| Ac | Acyl ($CH_3C(O)$—) |
| Aq. | Aqueous |
| Bn | Benzyl |
| C. | Celsius |
| calc. | Calculated |
| Celite | CELITE ™ diatomaceous earth |
| DCM | dichloromethane |
| Dess-Martin Periodinane | 1,1,1-tris(acetyloxy)-1,1-dihydro-1,2-benzodoxol-3-(1H)-one |
| DIEA | N,N-diisopropylethylamine |
| DMAP | 4-dimethylaminopyridine |
| DMDO | dimethyldioxirane |
| DMF | N,N-dimethylformamide |
| EDC | N-(3-dimethylaminopropyl)-N'-ethylcarbodiimide HCl |
| equiv. | Equivalent(s) |
| ES-MS | Electron Spray Ion-Mass Spectroscopy |
| EtOAc | Ethyl acetate |
| h | Hour(s) |
| HPLC | High performance liquid chromatography |
| min | Minute(s) |
| m.p. | Melting point |
| MS | Mass spectrum |
| Prep. | Preparative |
| r.t. (or rt) | Room temperature |
| sat. | Saturated |
| TBAI | tetrabutylammonium iodide |
| TBS | Tert-butyl dimethylsilyl |
| TEA | Triethyl amine |
| TEMPO | 2,26,6-tetramethy-1-piperidinyloxy free radical |
| TFA | Trifluoroacetic acid |
| THF | Tetrahydrofuran |
| Tlc | Thin layer chromatography |
| UDPGA | Uridine-5'-diphosphoglucuronic acid |

The general Schemes below illustrate a method for the syntheses of compounds of the present invention. All substituents and variables (e.g., $R^1$, $R^2$, $Ar^1$, v, w, etc.) are as defined above in Formula I unless indicated otherwise.

In Scheme I, I-1 is treated with a terminal alkyne of type I-2 in the presence of a suitable palladium catalyst such as tetrakistriphenylphosphine palladium(0) or [1,1'-bis(diphenylphosphino)ferrocene]dichloropalladium(II) or the like, and copper(I) iodide. The reaction is usually performed in an inert organic solvent such as DMF, between room temperature and 100° C., for a period of 6-48 h, and the product is an internal alkyne of structural formula I-3. Alkyne I-2 may contain a radioactive atom such as $^{35}S$ to provide the corresponding radiolabeled adduct upon reaction with I-1. Conversion of I-3 to -I-4 can be achieved by hydrogenation of the triple bond in the $R^9$ position, followed by treating I-3 with guanidine and triethylamine in methanol to selectively remove the phenolic acetate; then converting the phenol to the triflate I-4 via treatment with bis(trifluoromethylsulfonyl) amino pyridine in the presence of either triethylamine or N,N diisopropyl-N-ethyl amine in dichloromethane medium. Incorporation of the glycoside is completed by palladium assisted coupling of the triflate I-4 with the fully protected alkynyl-sugar I-5; for example, PG may be benzyl. In this method, I-4 is treated with an alkynyl sugar of type I-5 in the presence of a suitable palladium catalyst such as tetrakistriphenylphosphine palladium(0) and copper(I) iodide with an initiator such as tetrabutylammonium iodide. The reaction is usually performed in an inert organic solvent such as DMF, at 50° C., for a period of 1 to 5 hrs, and the product is a C-glycoside of structure I-6. Hydrogenation of the triple bond occurs along with the removal of the benzyl protected ethers by treatment with 10% palladium on carbon catalyst under hydrogen atmosphere in a solvent such as ethyl acetate reacting over 15-24 hours to form I-7 wherein $R^{14}$ is —$CH_2OH$. Ethers (wherein $R^{14}$ is —$CH_2O(CH_2)_y$—$R^{15}$) can be prepared by treatment with alkylating reagents and an appropriate base or using diazoalkane reagents and an appropriate metal catalyst such as $Rh_2(OAc)_2$. When R and/or $R^2$ is an acetate, deprotection with potassium cyanide in methanol heated to 50° C. for 1-2 hours affords the free hydroxyl group at those positions.

The process depicted in Scheme I can also be performed using HC≡C—$COOC_{1-6}$alkyl or HC≡C—$C(O)NR^{10}R^{11}$ in place of I-2, and the alkyl ester can be hydrolyzed to form compounds wherein $R^9$ is —C≡C—COOH.

SCHEME I

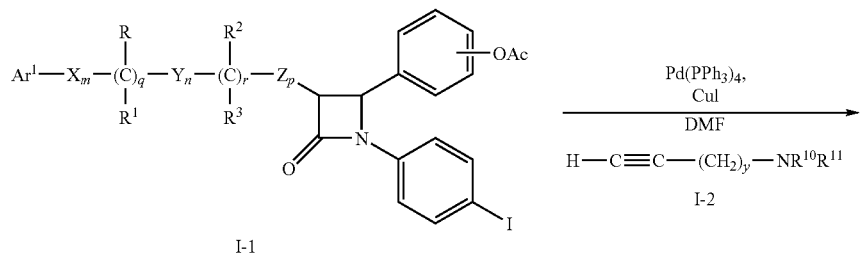

I-1

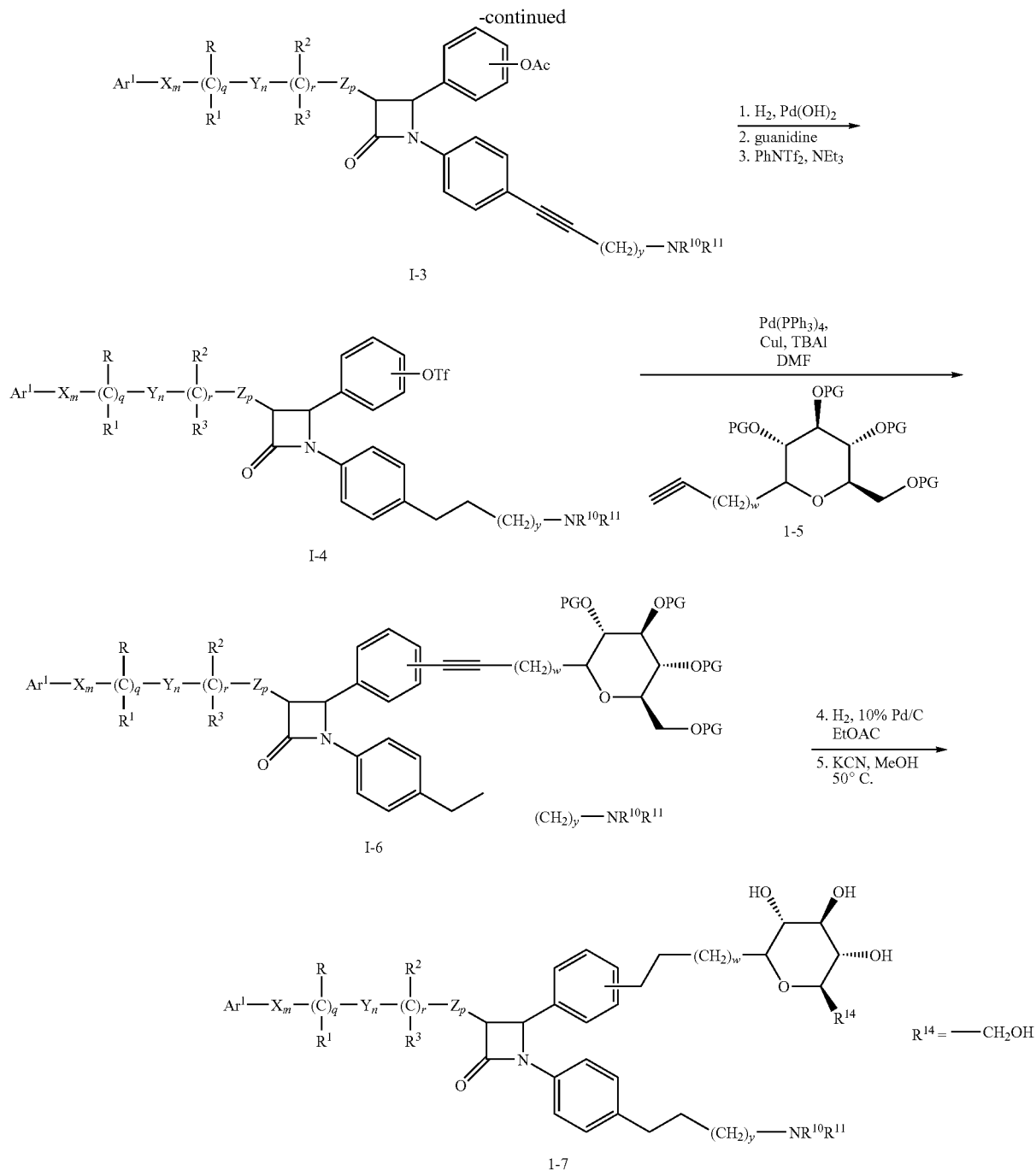

The conversion of the hydroxyl methyl C-glycoside I-6 to the corresponding C-glycoside carboxylate II-2 and the synthesis of amide analogs II-3 is shown in Scheme II. Starting with the intermediate I-6 shown in Scheme I, the removal of the benzyl protection and hydrogenation of the alkyne is completed by treating I-6 with 10% palladium on carbon under hydrogen atmosphere in a solvent such as ethyl acetate for 15-24 hours at room temperature. The primary hydroxyl group of II-1 is then selectively oxidized by using TEMPO free radical with sodium hypochlorite in the presence of KBr, tetrabutylammonium chloride and a buffer aqueous solution of sodium bicarbonate and sodium chloride. An appropriate solvent, for example dichloromethane or others known to those skilled in the art, is also needed to make II-1 soluble for the reaction. When R and/or $R^2$ is an acetate, a final deprotection of the acetate to create R and/or $R^2$ as hydroxyl is performed as described in Scheme I to afford the final C-glycoside carboxylate II-2. Amide analogs, such as those depicted by II-3, can thus be synthesized from the glycoside carboxylate by using standard EDC coupling procedures with various primary and secondary amines. Likewise, ester analogs (wherein $R^{14}$ is —$COOC_{1-6}$alkyl) can be made from II-2 using the appropriate alkyl alcohol.

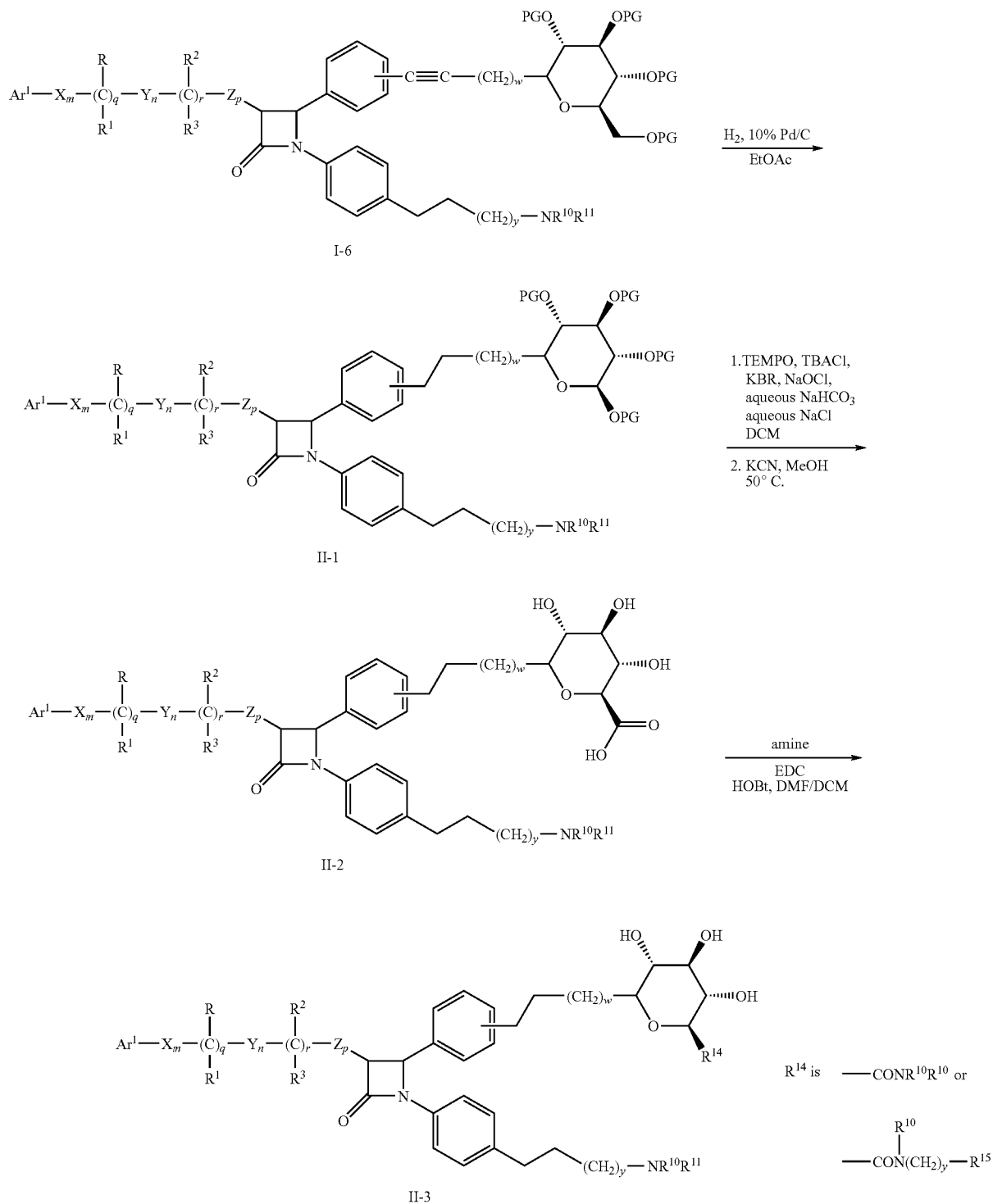

SCHEME II

The procedure for synthesizing I-6 described in Scheme I can be followed except omitting the step of hydrogenation of the triple bond in the $R^9$ position to form III-2, depicted in Scheme III. Then, for example, if benzyl protecting groups are employed they may be removed by treatment with excess ferric chloride in a suitable solvent such as dichloromethane to afford III-3a. Oxidation of the primary alcohol of the resulting poly-hydroxylated III-3a using the standard TEMPO conditions described in Scheme II provides the carboxylic acid III-3b. If R and/or $R^2$ is an acetate in III-3a or III-3b, deprotection to afford R and/or $R^2$ as hydroxyl is performed by treatment with potassium cyanide as described in Scheme I.

SCHEME III

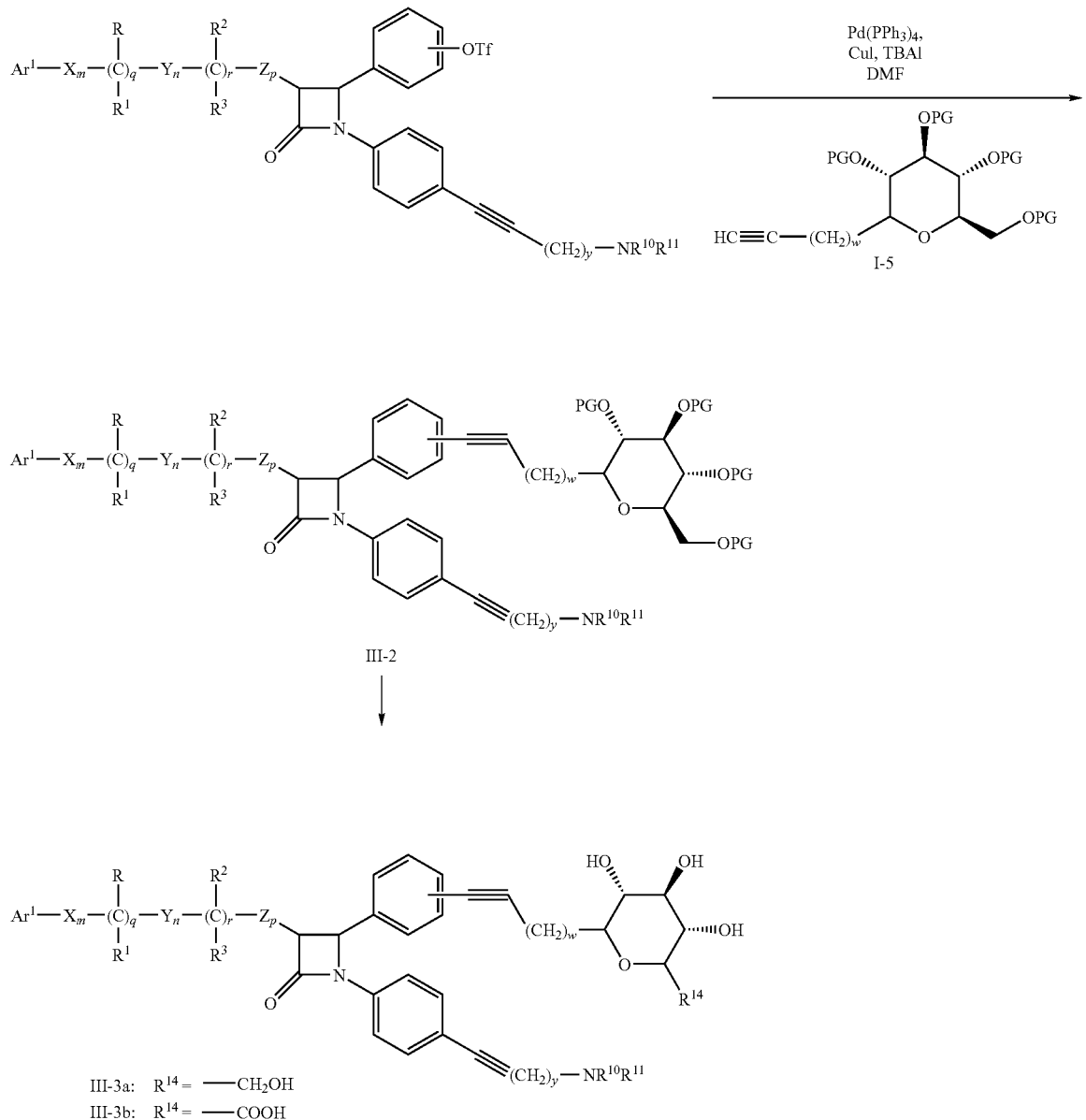

Alkenyl-linked sugar derivatives may also be synthesized using the conditions described in Scheme III, however using vinyl metal reagents to couple the alkenyl sugar moiety to intermediate III-1. Reagents such as the vinyl boronic acids derivatives of the alkenyl sugars may be cross coupled to intermediate III-1 via Suzuki reactions using suitable palladium catalysts in the presence of a suitable base such as triethylamine. The final alcohol compounds may then be prepared by deprotection, and the carboxylic acid derivative may be prepared by further functional group manipulations using procedures similar to those described above in earlier schemes.

As shown in Scheme IV, incorporation of the glycoside directly to the phenyl ring may be achieved by palladium assisted coupling of the triflate I-4 with a fully protected alkenyl stannyl-sugar intermediate, such as IV-1. The reaction may be performed in an inert organic solvent such as DMF or toluene with heating for a period of 1-24 h in the presence of a palladium catalyst such as $PdCl_2(PPh_3)_2$ or Pd(tetrakisPPh$_3$) to afford the product IV-2. Epoxidation of the double bond, with a reagent such as dimethyldioxirane (DMDO), followed by silane reduction, with a reagent such as triethylsilane (TES) or triisopropylsilane (TIS), provides the C-glycoside, IV-3. Removal of the protecting groups, e.g. benzyl protecting groups, by treatment with 10% palladium on carbon catalyst under hydrogen atmosphere in a solvent such as ethyl acetate over 15-24 hours affords IV-4. Alternatively, if intermediate III-1 is used in place of I-4, excess ferric chloride can be used for the deprotection step to obtain the alkynyl analog of IV-4. If R and/or $R^2$ is an acetate, deprotection to afford R and/or $R^2$ as hydroxyl is performed as described previously.

SCHEME IV

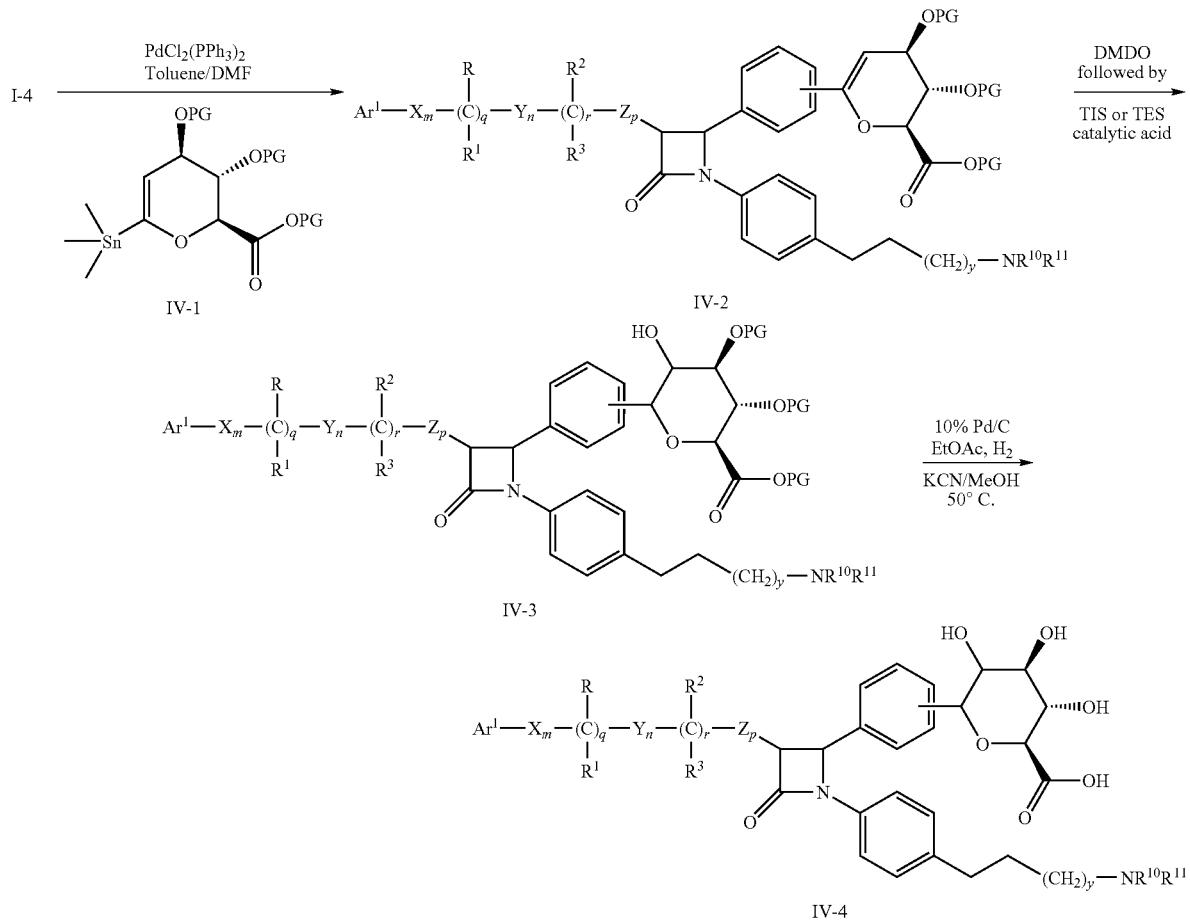

As shown in Scheme V, compounds of structural formula V-2 can be obtained by treating the alkenyl sugar intermediate V-1 with 9-borabicyclo[3.3.1]nonane (9-BBN) to form the alkyl borate ester, which upon palladium catalyzed cross-coupling with the triflate I-4 affords the protected C-glycoside V-2. The final product V-3 may then be prepared using procedures similar to those previously described in Schemes I and IV.

SCHEME V

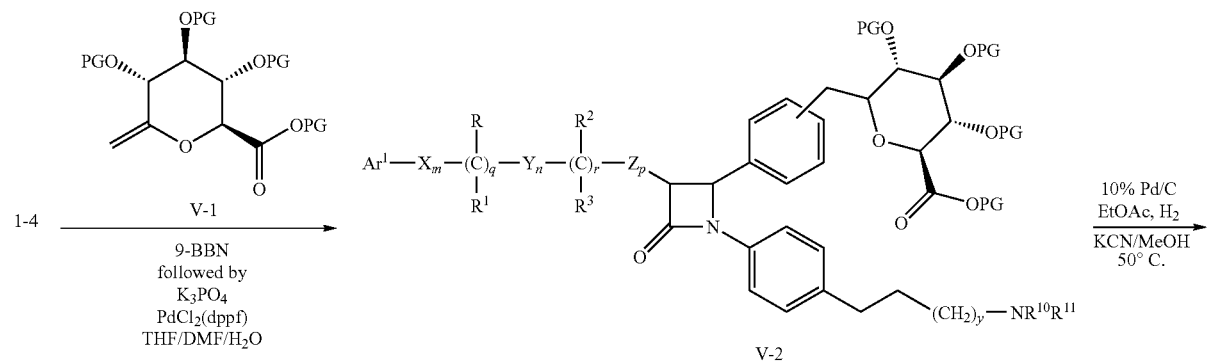

The compound (3R,4S)-3-[(3S)-3-(4-fluorophenyl)-3-hydroxypropyl]-4-(4-hydroxyphenyl)-1-(4-iodophenyl)azetidin-2-one (i-7) was prepared according to Burnett, D. S.; Caplen, M. A.; Domalski, M. S.; Browne, M. E.; Davis, H. R. Jr.; Clader, J. W. *Bioorg. Med. Chem. Lett.* (2002), 12, 311. Compound i-8 is the hydroxy-protected analog of i-7, where the protecting group is acyl.

Within the following synthetic examples, reference to an intermediate from a prior step is a reference to an intermediate compound made in a prior step within the same example, unless otherwise noted.

Preparation of N-prop-2-yn-1-ylacetamide (i-1):

Acetyl chloride (0.52 mL, 7.3 mmol) was added to a stirred solution of propargylamine (0.5 mL, 7.3 mmol) and dimethylaminopyridine (18 mg, 0.14 mmol) in pyridine (2.5 mL) at 0° C., and the resulting mixture was allowed to warm to ambient temperature. After approximately 15 h, the reaction mixture was diluted with ethyl acetate and washed successively with 1N HCl and brine. The organic phase was dried (Na$_2$SO$_4$), filtered and concentrated in vacuo to afford the title compound (i-1), which was used without further purification.

Preparation of N-prop-2-yn-1-ylbenzenesulfonamide (i-2):

Benzene sulfonyl chloride (1.16 mL, 9.1 mmol) was added to stirred solution of propargylamine (0.62 mL, 9.1 mmol) and dimethylaminopyridine (22 mg, 0.18 mmol) in pyridine (5 mL) at room temperature. The resulting solution was aged at ambient temperature for approximately 15 h. The reaction mixture was diluted with ethyl acetate and washed successively with 1N HCl and brine. The organic phase was dried (Na$_2$SO$_4$), filtered and concentrated in vacuo to furnish the title compound (i-2), which was used without further purification.

Preparation of N,N-Dimethyl-N'-prop-2-yn-1-ylurea (i-3):

Dimethyl carbamylchloride (0.84 mL, 9.1 mmol) was added to a stirred solution of propargylamine (0.62 mL, 0.1 mmol) and dimethylaminopyridine (22 mg, 0.18 mmol) in pyridine (5 mL) at room temperature. The resulting suspension was stirred at ambient temperature for approximately 15 h. The reaction mixture was diluted with ethyl acetate and washed successively with 1N HCl and brine. The organic phase was dried (Na$_2$SO$_4$), filtered and concentrated in vacuo to afford the title compound (i-3), which was used without further purification.

Preparation of N-Methyl-N-prop-2-yn-1-ylmethanesulfonamide (i-4):

Methansulfonylchloride (1.12 mL, 14.5 mmol) was added to a stirred solution of N-methylpropargylamine (1.22 mL, 14.5 mmol) and dimethylaminopyridine (35 mg, 0.30 mmol) in pyridine (10 mL) at room temperature. After aging for approximately 15 h, the reaction mixture was poured into ethyl acetate and washed successively with 1N HCl and brine. The organic phase was dried (Na$_2$SO$_4$), filtered and concentrated in vacuo, to afford the title compound (i-4), which was used without further purification.

Preparation of N-prop-2-yn-1-ylmethanesulfonamide (i-5):

Methansulfonylchloride (1.40 mL, 18.1 mmol) was added dropwise to a stirred solution of propargylamine (1.00 g, 18.1 mmol) and dimethylaminopyridine (44.0 mg, 0.36 mmol) in pyridine (10 mL) at 0° C. After aging for approximately 15 h, the reaction mixture was poured into 1N HCl and extracted twice with ethyl acetate. The combined organic extracts were washed with saturated aqueous sodium bicarbonate, brine, dried (MgSO$_4$), filtered and concentrated in vacuo, to afford the title compound i-5. Crude i-5 crystallized on standing and was used without further purification.

Preparation of 3,7-anhydro-4,5,6,8-tetra-Oβ-benzyl-1,2-dideoxy-D-glycero-D-gulo-oct-1-ynitol (i-6):

romethane (100 mL) cool to −78° C. was added DMSO (2.6 mL, 37.00 mmol) and the resulting solution stirred for 15 minutes. A solution of 2,3,4,6-tetra-O-benzyl-β-D-glucopyranose (6 g, 11.10 mmol) in dichloromethane (10 mL) was added via syringe and the resulting mixture was stirred for 1 hour at −78° C. Finally, triethylamine (6.4 mL, 46.24 mmol) was added and the mixture was stirred for 1 hour allowing to warm to room temperature. Diluted with ethyl acetate (200 mL) and washed with 0.5 M HCl (2×75 mL), water (1×75 mL) and brine (1×75 mL). The organics were dried over magnesium sulfate, filtered, and concentrated. The crude product was used without further purification. m/z (ES) 539 (M+H)$^+$.

STEP B, Preparation of i-6: To a solution of the lactone intermediate from Step A, (538 mg, 1.00 mmol) in anhydrous THF (5 mL) cooled to 0° C. was added 0.5 M ethylnyl magnesiumbromide (3.0 mL, 1.50 mmol) and the solution stirred for one hour. The mixture was concentrated and the residue dissolved in acetnitrile (1 mL). The solution was set under nitrogen and triethylsilane (320 µL, 2.0 mmol) was added to the mixture followed by boron trifluoro-etherate (127 µL, 1.0 mmol). The resulting solution was stirred at room temperature for 5 hours. Partitioned between ethyl acetate (25 mL) and aqueous saturated sodium bicarbonate (5 mL), the organics dried over sodium sulfate, filtered and concentrated in vacuo. Preparative TLC plate purification (6×1000 µM) eluting with 10% ethyl acetate/90% hexane afforded the title compound as a clear viscous liquid.

m/z (ES) 549 (M+H)$^+$. $^1$HNMR (500 MHz, CDCl$_3$) δ: 7.44-7.29 (m, 18H), 7.16-7.14 (m, 2H), 5.30 (d, J=10 Hz, 1H), 5.03 (d, J=10.4 Hz, 1H), 4.95-4.82 (m, 3H), 4.64 (d, J=12.0 Hz, 1H), 4.56 (d, J=12.3 Hz, 1H), 4.06 (dd, J=1.6, 7.3 Hz, 1H), 3.73 (ddd, J=1.7, 4.1, 10.8 Hz, 2H), 3.68-3.63 (m, 3H), 3.47-3.45 (m, 1H), 2.56 (d, J=2.0 Hz, 1H).

EXAMPLE 1

N-[3-(4-{(2S,3R)-2-(-(4-{[(2S, 5S, 3R, 4R, 6R)-3,4,5-trihydroxy-6-(hydroxymethyl)perhydro-2H-pyran-2-yl]ethyl-2-yl}phenyl)-3-[(3S)-3-(4-fluorophenyl)-3-hydroxypropyl]-4-oxoazetidin-1-yl}phenyl) propyl]-N-methylmethanesulfonamide Step A Preparation of 4-[(2S, 3R)-3-[(3S)-3-(acetyloxy)-3-(4-fluorophenyl)propyl]-1-(4-{3-[methyl(methylsulfonyl)amino]prop-1-yn-1-yl}phenyl)-4-oxoazetidin-2-yl]phenyl acetate (i-9 wherein R$^{10}$ is —CH$_3$)

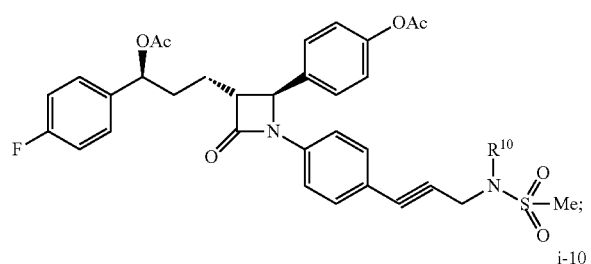

i-9

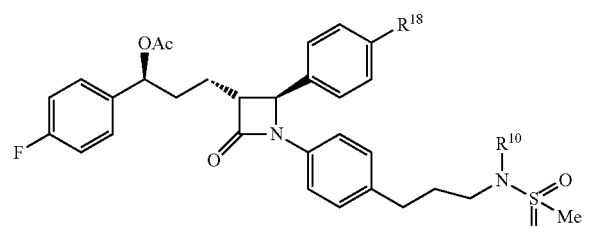

i-10 i-10a: R$^{18}$ is —OTf;    i-10b: R$^{18}$ is —OAc;

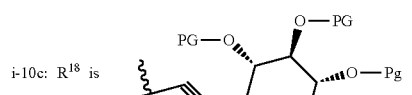

i-10c: R$^{18}$ is

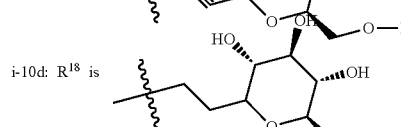

i-10d: R$^{18}$ is

STEP A, Preparation of glucosyl lactone intermediate: To a solution of oxalyl chloride (2.4 mL, 27.74 mmol) in dichlo-

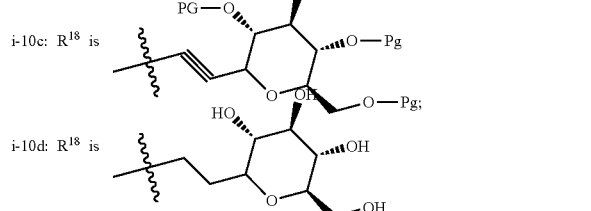

Dichlorobis(triphenylphosphine)palladium(II) (35 mg, 0.050 mmol) and copper(I) iodide (19 mg, 0.10 mmol) were added to a solution of i-8 (0.15 g, 0.25 mmol) and i-4 (44 mg, 0.30 mmol) in triethylamine (0.17 mL, 1.2 mmol) and DMF (1.3 mL). The reaction mixture was saturated with nitrogen and stirred at room temperature. After 14 h, the reaction mixture was quenched with saturated aqueous ammonium chloride and extracted three times with EtOAc. The combined organic extracts were washed with water, brine, dried (Na$_2$SO$_4$) and concentrated in vacuo. Purification of the crude residue by flash chromatography on silica gel (gradient elution; 20%-35% EtOAc/hexanes as eluent) afforded the title compound i-9 wherein R$^{10}$ is —CH$_3$. m/z (ES) 561 (M-OAc)$^+$. $^1$HNMR (500 MHz, CDCl$_3$) δ: 7.35 (d, J=8.5 Hz, 1H), 7.28 (dd, J=6.4, 8.4 Hz, 1H), 7.19 (d, J=8.1 Hz, 1H), 7.12 (d, J=8.5 Hz, 1H), 7.08 (d, J=8.2 Hz, 1H), 7.02 (dd, J=6.5, 8.6 Hz, 1H), 5.72 (t, 6.6 Hz, 1H), 4.62 (d, J=2.3 Hz, 1H), 4.15 (dd, J=7.1, 11 Hz, 1H), 3.15-3.12 (m, 2H), 3.08-3.05 (m, 1H), 2.84 (s, 3H), 2.78 (s, 3H), 2.60 (t, 7.4 Hz, 2H), 2.32 (s, 3H), 2.07 (overlapped s, 3H), 2.09-2.03 (m, 2H), 1.90-1.83 (m, 4H).

Step B

Preparation of 4-[(2S, 3R)-3-[(3S)-3-(acetyloxy)-3-(4-fluorophenyl)propyl]-1-(4-{3-[methyl(methylsulfonyl)amino]propyl}phenyl)-4-oxoazetidin-2-yl] phenyl acetate (i-10b wherein R$^{10}$ is CH$_3$)

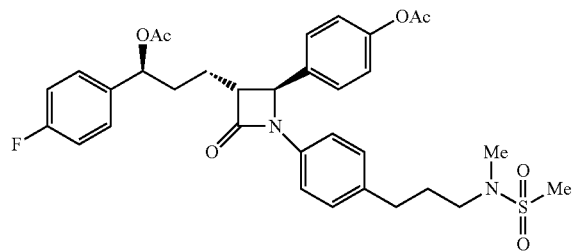

A mixture of the intermediate from Step A (805 mg, 1.30 mmol) and palladium hydroxide (150 mg of 20 wt. % on activated carbon) in EtOAc (25 mL) was hydrogenated at atmospheric pressure. After 8 h, the reaction mixture was filtered through a short column of Celite®, eluting copiously with EtOAc. The filtrate was concentrated in vacuo to afford the title compound. m/z (ES) 565 (M-OAc)$^+$. $^1$HNMR (500 MHz, CDCl$_3$) δ: 7.35 (d, J=8.5 Hz, 1H), 7.28 (dd, J=5.4, 8.4 Hz, 1H), 7.28-7.20 (m, 1H), 7.14 (d, J=6.6 Hz, 1H), 7.06 (d, J=8.5 Hz, 1H), 7.04 (dd, J=6.5, 8.6 Hz, 1H), 5.72 (t, 7.1 Hz, 1H), 4.64 (d, J=2.5 Hz, 1H), 4.28 (s, 2H), 3.10 (dt, J=2.4, 7.6 Hz, 1H), 2.99 (s, 3H), 2.94 (s, 3H), 2.33 (s, 3H), 2.08 (overlapped s, 3H), 2.09-2.03 (m, 2H), 1.90-1.83 (m, 4H).

Step C

Preparation of (1S)-1-(4-fluorophenyl)-3-[(3R, 4S)-1-(4-{3-[methyl(methylsulfonyl)amino] propyl}phenyl)-2-oxo-4-(4-{[(trifluoromethyl)sulfonyl]oxy}phenyl)azetidin-3-yl]propyl acetate (i-10a wherein R$^{10}$=CH$_3$)

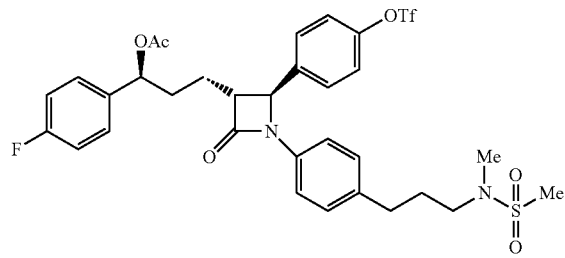

Guanidine (13 mg, 0.13 mmol) was added to a mixture of the intermediate from Step B (82 mg, 0.13 mmol) and triethylamine (18 μL, 0.13 mmol) in methanol (2 mL). After 3 h, the reaction mixture was quenched with saturated aqueous ammonium chloride and extracted three times with EtOAc. The combined organic extracts were washed with water, brine, dried (Na$_2$SO$_4$) and concentrated in vacuo to afford a clear oil which was dissolved in DCM (1.5 mL). Triethylamine (24 mL, 0.17 mmol), DMAP (2.0 mg, 0.016 mmol) and (bis(trifluoromethylsulfonyl)amino pyridine (77 mg, 0.13 mmol) were added successively to the above solution. After 3 h, the reaction was quenched with 0.5 N HCl and extracted three times with EtOAc. The combined organic extracts were washed with water, brine, dried (Na$_2$SO$_4$) and concentrated in vacuo. Purification of the crude residue by flash chromatography on silica gel (gradient elution; 35%-40% EtOAc/hexanes as eluent) afforded the title compound. m/z (ES) 655 (M-OAc)$^+$. $^1$HNMR (500 MHz, CDCl$_3$) δ: 7.43 (d, J=8.6 Hz, 1H), 7.32-7.28 (m, 2H), 7.15 (d, J=6.4 Hz, 1H), 7.10 (d, J=8.4 Hz, 1H), 7.04 (t, J=6.5 Hz, 1H), 5.72 (t, 6.6 Hz, 1H), 4.66 (d, J=2.3 Hz, 1H), 3.14 (dt, J=2.6, 6.6 Hz, 2H), 3.08 (dt, J=2.5, 8.2 Hz, 1H), 2.84 (s, 3H), 2.79 (s, 3H), 2.61 (t, 7.7 Hz, 2H), 2.08 (overlapped s, 3H), 2.09-2.04 (m, 2H), 1.93-1.84 (m, 4H).

Step D

Preparation of intermediate i-10c wherein R$^{10}$ is —CH$_3$, and PG is benzyl

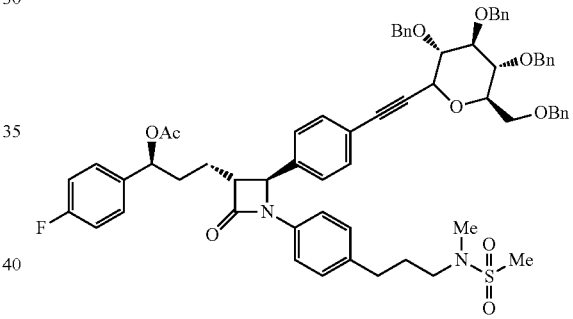

To an oven dried flask was added CuI (30 mg, 0.16 mmol), tetrabutylammonium iodide (TBAI) (130 mg, 0.35 mmol), and the intermediate from Step C (250 mg, 0.35 mmol). The charged flask was set under nitrogen atmosphere and a solution of i-6 (384 mg, 0.70 mmol) in DMF (2.5 mL) was added to the mixture followed by TEA (342 μL, 2.40 mmol). The flask was then equipped with a condensor, and the mixture was evacuated and set under nitrogen several times in efforts to de-gas the solvent. Pd(PPh$_3$)$_4$ (246 mg, 0.22 mmol) was then added to the reaction and the reaction mixture was heated to 70° C. for 1.5 hours. TLC provided that there was no starting material. The reaction was quenched with 0.1N HCl (7.5 mL) and diluted with ethyl acetate (15 mL), The mixture was partitioned with ethyl acetate (2×15 mL), the organic layers were combined, washed with brine, dried over magnesium sulfate, filtered and concentrated. Purification was done by preparative TLC plate (4 plates, 1000 μm) eluting with 70% ethyl acetate/hexane to afford the title compound. m/z (ES) 1053 (M-OAc)$^+$. $^1$HNMR (500 MHz, CDCl$_3$) δ: 7.46 (d, J=8.3 Hz, 1H), 7.40-7.28 (m, 22H), 7.18-7.14 (m, 2H), 7.10-7.04 (m, 2H), 5.72 (t, 6.7 Hz, 1H), 5.06 (d, J=10.5 Hz, 1H), 4.95 (d, J=11.0 Hz, 1H), 4.86 (app t, J=9.3 Hz, 2H), 4.65 (d, J=12.2 Hz, 1H), 4.61-4.54 (m, 2H), 4.30 (d, J=8.7 Hz, 1H), 3.81-3.66 (m, 4H), 3.55-3.50 (m, 1H), 3.14 (dt, J=2.3, 7.1 Hz, 2H), 3.08 (dt, J=2.3, 8.2 Hz, 1H), 2.84 (s, 3H), 2.79 (s, 3H), 2.61 (t, 7.7 Hz, 2H), 2.08 (overlapped s, 3H), 2.09-2.04 (m, 2H), 1.93-1.84 (m, 4H).

Step E

Preparation of i-10d wherein $R^{10}$ is —$CH_3$

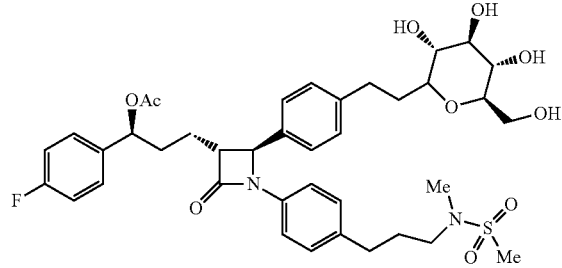

To a solution of the intermediate from Step D (250 mg, 0.23 mmol) in ethyl acetate (6 mL) was added 10% palladium on carbon (125 mg) and the resulting suspension set under hydrogen atmosphere and stirred vigorously overnight (15 hr). TLC exhibited 60% completed, therefore another 65 mg of catalyst was added and the suspension re-subjected to the hydrogen atmosphere for 6 hours (monitored every hour until completed). The catalyst was filtered off by using a Gilmen 0.45 μM PTFE syringe filter disc and washed with ethyl acetate (3×5 mL). The filtrate was concentrated in vacuo and the residue purified by preparative TLC plates eluting with 12% methanol/88% dichloromethane to afford the title compound.

m/z (ES) 697 (M-OAc)+. $^1$HNMR (500 MHz, $CD_3OD$) δ: 7.35-7.30 (m, 2H), 7.28-7.25 (m, 4H), 7.18 (d, J=8.5 Hz, 2H), 7.14 (d, J=8.4 Hz, 2H), 7.06 (app, t, J=8.7 Hz, 2H), 5.71 (br dd, J=6.3, 8.0 Hz, 1H), 4.80 (d, J=2.3 Hz, 1H), 3.85 (dd, J=2.3, 11.8 Hz, 1H), 3.64 (dd, J=6.0, 11.9 Hz, 1H), 3.27-3.22 (m, 2H), 3.18-3.14 (m, 1H), 3.12-3.04 (m, 4H), 2.90-2.85 (m, 1H) 2.80 (s, 3H), 2.79 (s, 3H), 2.75-2.70 (m, 1H), 2.55 (t, 7.7 Hz, 2H), 2.15-2.05 (m, 2H), 2.03 (s, 3H), 1.85-1.80 (m, 4H), 1.75-1.68 (m, 1H).

Step F

N-[3-(4-{(2S,3R)-2-(-(4-{[(2S, 5S, 3R, 4R, 6R)-3,4,5-trihydroxy-6-(hydroxymethyl)perhydro-2H-pyran-2-yl]ethyl-2-yl}phenyl)-3-[(3S)-3-(4-fluorophenyl)-3-hydroxypropyl]-4-oxoazetidin-1-yl}phenyl)propyl]-N-methylmethanesulfonamide

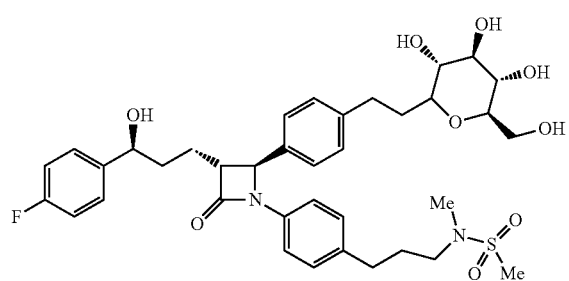

To a solution of the intermediate from Step E (60 mg, 0.08 mmol) in methanol (2 mL) was added potassium cyanide (0.5 mg, 0.008 mmol) and the resulting solution stirred at 50° C. for 2 hours. The solution was concentrated and the residue purified by preparative TLC plate eluding with 15% methanol/85% dichloromethane to afford the title compound. m/z (ES) 697 (M-OAc)+ and 737 (M+Na)+)+. $^1$HNMR (500 MHz, $CD_3OD$) δ: 7.35-7.30 (m, 2H), 7.28-7.25 (m, 4H), 7.18 (d, J=8.5 Hz, 2H), 7.12 (d, J=8.4 Hz, 2H), 7.03 (app, t, J=8.6 Hz, 2H), 4.80 (br d, J=2.03 Hz, 1H), 4.60 (br dd, J=5.0, 7.1 Hz, 1H), 3.86 (dd, J=2.1, 11.9 Hz, 1H), 3.64 (dd, J=6.0, 12.0 Hz, 1H), 3.27-3.22 (m, 2H), 3.18-3.14 (m, 1H), 3.12-3.04 (m, 4H), 2.90-2.82 (m, 1H) 2.80 (s, 3H), 2.79 (s, 3H), 2.77-2.70 (m, 1H), 2.58 (t, 7.6 Hz, 2H), 2.16-2.08 (m, 1H), 1.98-1.80 (m, 6H), 1.74-1.66 (m, 1H).

EXAMPLE 2

N-[3-(4-{(2S,3R)-2-(4-{[(2S, 5S, 3R, 4R, 6S)-3,4,5-trihydroxy-6-(carboxy)perhydro-2H-pyran-2-yl]ethyl-2-yl}phenyl)-3-[(3S)-3-(4-fluorophenyl)-3-hydroxypropyl]-4-oxoazetidin-1-yl}phenyl)propyl]-N-methylmethanesulfonamide Step A Preparation of 8-{4-[(2S,3R)-3-[(3S)-3-(acetyloxy)-3-(4-fluorophenyl)propyl]-1-(4-{3-[methyl(methylsulfonyl)amino]propyl}phenyl)-4-oxoazetidin-2-yl]phenyl}-2,6-anhydro-7,8-dideoxy-L-gulo-octanic acid

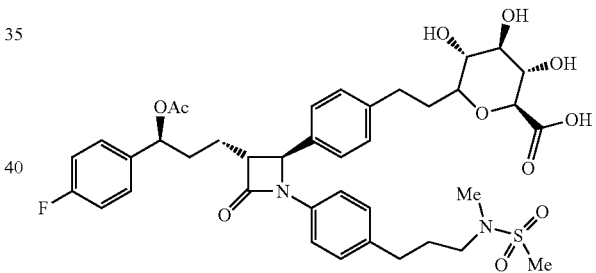

To a solution of i-10d wherein $R^{10}$ is —$CH_3$ (76 mg, 0.100 mmol) in dichloromethane (1 mL) was added 2,2,6,6 TEMPO free radical (0.3 mg, 0.002 mmol) followed by a preformed mixture of tetrabutylammonium chloride (2.3 mg, 0.008 mmol) and KBr (2.0 mg, 0.016 mmol) in saturated aqueous solution of sodium bicarbonate (320 μL). The mixture was cooled to 0° C. via ice/water bath and stirred vigorously. A solution of aqueous saturated sodium bicarbonate (190 μL), aqueous saturated sodium chloride (320 μL) and NaOCl (70 μL of a 0.6 M solution) was added dropwise via syringe and the resulting solution stirred for 2 hours allowing to warm to room temperature. The solution was transferred to a separatory funnel and extracted with dichloromethane (2×10 mL). The organics were combined, dried over magnesium sulfate, filtered and concentrated in vacuo. Purification was done by Gilson reverse phase HPLC eluting with a gradient of 25-75% acetonitrile/water (0.1% TFA buffer) over 15 minutes to afford the title compound. m/z (ES) 711 (M-OAc)+ $^1$HNMR (500 MHz, $CD_3OD$) δ: 7.35-7.30 (m, 2H), 7.28 (d, J=8.2 Hz, 2H), 7.24 (d, J=8.0 Hz, 2H), 7.18 (d, J=8.7 Hz, 2H), 7.12 (d, J=8.5 Hz, 2H), 7.03 (app t, J=8.7 Hz, 2H), 5.71 (dd, J=6.0, 7.5 Hz, 1H), 4.80 (br d, J=2.2 Hz, 1H), 3.68 (d, J=9.6 Hz, 1H), 3.50 (t, J=9.4 Hz, 1H), 3.30-3.22 (m, 2H), 3.18-3.05 (m, 5H), 2.88-2.82 (m, 1H) 2.80 (s, 3H), 2.79 (s, 3H), 2.75-2.66 (m, 1H), 2.58 (t, 7.6 Hz, 2H), 2.18-2.06 (m, 2H), 2.04 (s, 3H), 1.94-1.88 (m, 1H), 1.86-1.80 (m, 4H).

Step B

N-[3-(4-{(2S,3R)-2-(4-{[(2S, 5S, 3R, 4R, 6S)-3,4,5-trihydroxy-6-(carboxy)perhydro-2H-pyran-2-yl]ethyl-2-yl}phenyl)-3-[(3S)-3-(4-fluorophenyl)-3-hydroxypropyl]-4-oxoazetidin-1-yl}phenyl)propyl]-N-methylmethanesulfonamide

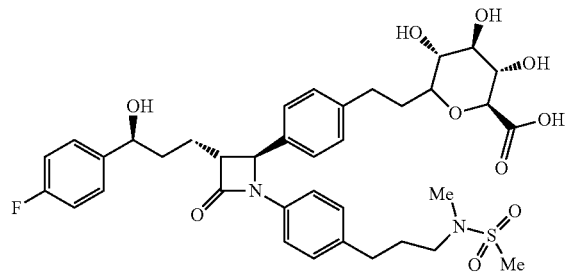

To a solution of the intermediate from Step A above (40 mg, 0.05 mmol) in methanol (1.5 mL) was added potassium cyanide (0.35 mg, 0.005 mmol) and the resulting solution stirred at 50° C. for 2 hours. The solution was concentrated and the residue purified by Gilson reverse phase HPLC eluting with a gradient of 25-75% acetonitrile/water (0.1% TFA buffer) over 15 minutes to afford the title compound. m/z (ES) 711 (M-OAcOH)$^+$ and 729 (M+H)$^+$ $^1$HNMR (500 MHz, CD$_3$OD) δ: 7.35-7.30 (m, 2H), 7.28 (d, J=8.2 Hz, 2H), 7.24 (d, J=8.0 Hz, 2H), 7.18 (d, J=8.7 Hz, 2H), 7.12 (d, J=8.5 Hz, 2H), 7.03 (app t, J=8.7 Hz, 2H), 4.79 (br d, J=2.1 Hz, 1H), 4.60 (br dd, J=5.0, 7.01 Hz, 1H), 3.664 (d, J=9.9 Hz, 1H), 3.48 (t, J=9.3 Hz, 1H), 3.30-3.22 (m, 2H), 3.18-3.03 (m, 5H), 2.90-2.82 (m, 1H) 2.79 (s, 3H), 2.78 (s, 3H), 2.77-2.75 (m, 1H), 2.71-2.64 (m, 1H), 2.58 (t, 7.6 Hz, 2H), 2.16-2.08 (m, 1H), 1.98-1.80 (m, 6H), 1.74-1.66 (m, 1H).

EXAMPLE 3

N-[3-(4-{(2S,3R)-2-(-(4-{[(2S, 5S, 3R, 4R, 6R)-3,4,5-trihydroxy-6-(hydroxymethyl)perhydro-2H-pyran-2-yl]ethyl-2-yl}phenyl)-3-[(3S)-3-(4-fluorophenyl)-3-hydroxypropyl]-4-oxoazetidin-1-yl}phenyl)propyl]methanesulfonamide Step A Preparation of 4-[(2S, 3R)-3-[(3S)-3-(acetyloxy)-3-(4-fluorophenyl)propyl]-1-(4-{3-[(methylsulfonyl)amino]prop-1-yn-1-yl}phenyl)-4-oxoazetidin-2-yl]phenyl acetate (i-9 wherein R$^{10}$ is —H)

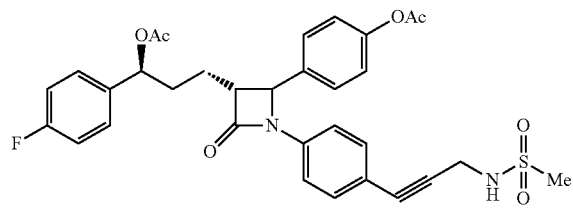

Dichlorobis(triphenylphosphine)palladium(II) (125 mg, 0.17 mmol) and copper(I) iodide (63 mg, 0.33 mmol) were added to a solution of i-8 (1.0 g, 1.66 mmol) and i-5 (333 mg, 2.50 mmol) in triethylamine (1.63 mL, 11.62 mmol) and DMF (15 mL). The reaction mixture was saturated with nitrogen and stirred at room temperature. After 2 h, the reaction mixture was quenched with saturated aqueous ammonium chloride and extracted three times with EtOAc. The combined organic extracts were washed with water, brine, dried (Na$_2$SO$_4$) and concentrated in vacuo. Purification of the crude residue by Horizon MPLC (40=silica column) with stepwise gradient elution; (0-50% EtOAc/hexanes as eluent) afforded the title compound. m/z (ES) 547 (M-OAc)$^+$. $^1$HNMR (500 MHz, CDCl$_3$) δ: 7.35 (d, J=8.4 Hz, 1H), 7.28 (dd, J=6.4, 8.4 Hz, 1H), 7.19 (d, J=8.5 Hz, 1H), 7.12 (d, J=8.5 Hz, 1H), 7.08 (d, J=8.3 Hz, 1H), 7.02 (dd, J=6.5, 8.6 Hz, 1H), 5.72 (t, 6.6 Hz, 1H), 4.60 (d, J=2.3 Hz, 1H), 4.21-4.16 (m, 1H), 4.15 (overlapped dd, J=7.1, 11 Hz, 1H), 3.15-3.12 (m, 2H), 3.09-3.04 (m, 1H), 2.96 (s, 3H), 2.58 (t, 7.6 Hz, 2H), 2.30 (s, 3H), 2.07 (overlapped s, 3H), 2.09-2.03 (m, 2H), 1.90-1.83 (m, 4H).

Step B

Preparation of 4-[(2S, 3R)-3-[(3S)-3-(acetyloxy)-3-(4-fluorophenyl)propyl]-1-(4-{3-[(methylsulfonyl)amino]propyl}phenyl)-4-oxoazetidin-2-yl]phenyl acetate (i-10b wherein R$^{10}$ is —H)

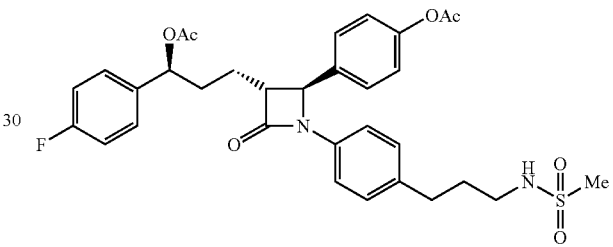

A mixture of the intermediate from Step A (300 mg, 0.50 mmol) and both 10% palladium on activated carbon (50 mg) and 20% palladium hydroxide on activated carbon (25 mg) in EtOAc (9 mL) was hydrogenated at atmospheric pressure. After 15 h, the reaction mixture was filtered through a Gilmen 0.45 μM PTFE syringe filter and the filtered catalyst washed several times with with EtOAc. The filtrate was concentrated in vacuo and the residue purified by preparative TLC plate (1000 μM, silica gel) to afforded the title compound. m/z (ES) 551 (M-OAc)$^+$.

Step C

Preparation of (1S)-1-(4-fluorophenyl)-3-[(3R, 4S)-1-(4-{3-[(methylsulfonyl)amino]propyl}phenyl)-2-oxo-4-(4-{[(trifluoromethyl)sulfonyl]oxy}phenyl)azetidin-3-yl]propyl acetate (i-10a wherein R$^{10}$ is —H)

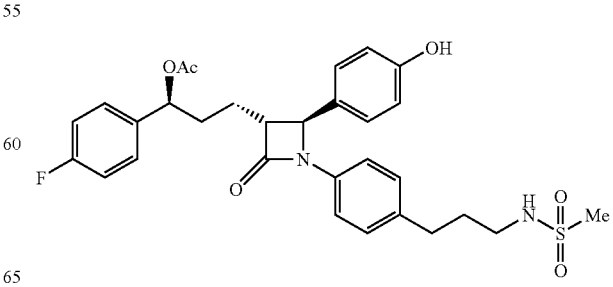

Guanidine (33 mg, 0.34 mmol) was added to a mixture of the intermediate from Step B, (210 mg, 0.34 mmol) and triethylamine (48 μL, 0.34 mmol) in methanol (4 mL). After 3 h, the reaction mixture was quenched with saturated aqueous ammonium chloride and extracted three times with EtOAc. The combined organic extracts were washed with water, brine, dried ($Na_2SO_4$) and concentrated in vacuo to afford a clear oil which was dissolved in DCM (3 mL). Triethylamine (62 μL, 0.34 mmol), DMAP (4.0 mg, 0.034 mmol) and (bis(trifluoromethylsulfonyl)amino pyridine (202 mg, 0.34 mmol) were added and the resulting solution stirred for 3 h at room temperature. The reaction was quenched with 0.5 N HCl and extracted three times with EtOAc. The combined organic extracts were washed with water, brine, dried ($Na_2SO_4$) and concentrated in vacuo. Purification of the crude residue by preparative TLC plate (elution; 40% EtOAc/hexanes) afforded the title compound. m/z (ES) 641 (M-OAc)+.

Step D

Preparation of i-10c wherein $R^{10}$ is —H and PG is benzyl

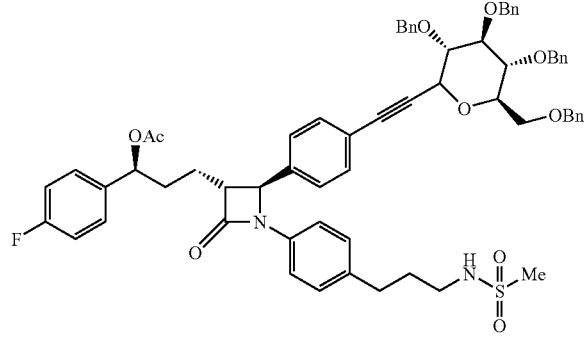

To an oven dried flask was added CuI (6 mg, 0.03 mmol), TBAI (27 mg, 0.07 mmol), and the intermediate from Step C, (50 mg, 0.07 mmol). The charged flask was set under nitrogen atmosphere and a solution of i-6 (75 mg, 0.14 mmol) in DMF (0.5 mL) was added to the mixture followed by TEA (70 μL, 0.5 mmol). The flask was then equipped with a condensor, and the mixture was evacuated and set under nitrogen several times in effort to de-gass the solvent. $Pd(PPh_3)_4$ (28 mg, 0.02 mmol) was then added to the reaction and the reaction mixture was heated to 70° C. for 1.5 hours. TLC proved that there was no starting material. The reaction was quenched with 0.1N HCl (5 mL) and diluted with ethyl acetate (15 mL), then partitioned with ethyl acetate (2×15 mL). The organic layers were combined, washed with brine, dried over magnesium sulfate, filtered and concentrated. Purification was done by preparative TLC plate (1000 μM) eluting with 70% ethyl acetate/hexane to afford the title compound. m/z (ES) 1039 (M-OAc)+. $^1$HNMR (500 MHz, $CDCl_3$) δ: 7.46 (d, J=8.3 Hz, 1H), 7.40-7.28 (m, 22H), 7.18-7.14 (m, 2H), 7.10-7.04 (m, 2H), 5.72 (t, 6.8 Hz, 1H), 5.06 (d, J=10.6 Hz, 1H), 4.95 (d, J=11.0 Hz, 1H), 4.86 (app t, J=9.1 Hz, 2H), 4.65 (d, J=12.0 Hz, 1H), 4.61-4.54 (m, 2H), 4.30 (d, J=8.7 Hz, 1H), 4.18-4.12 (m, 1H), 3.81-3.66 (m, 4H), 3.55-3.50 (m, 1H), 3.14 (dd, J=6.9, 12.5 Hz, 2H), 3.08 (dt, J=2.3, 8.2 Hz, 1H), 2.93 (s, 3H), 2.63 (t, 7.6 Hz, 2H), 2.08 (overlapped s, 3H), 2.09-2.04 (m, 2H), 1.93-1.84 (m, 4H), 1.32-1.28 (m, 3H).

Step E

Preparation of i-10d wherein $R^{10}$ is —H

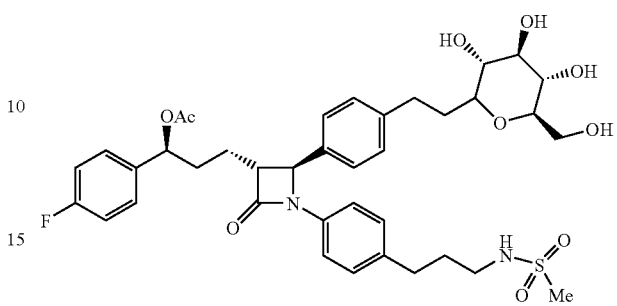

To a solution of the intermediate from Step D, (45 mg, 0.04 mmol) in ethyl acetate (1 mL) was added 10% palladium on carbon (45 mg) and the resulting suspension set under hydrogen atmosphere and stirred vigorously overnight (15 hr). TLC exhibited 80% completed, therefore another 35 mg of catalyst was added and the suspension re-subjected to the hydrogen atmosphere for 3 hours (monitored every hour until completed). The catalyst was filtered off by using a Gilmen 0.45 μM PTFE syringe filter disc and washed with ethyl acetate (3×5 mL). The filtrate was concentrated in vacuo and the residue purified by preparative TLC plates eluding with 12% methanol/88% dichloromethane to afford the title compound. m/z (ES) 683 (M-OAc)+. $^1$HNMR (500 MHz, $CD_3OD$) δ: 7.35-7.30 (m, 2H), 7.28-7.25 (m, 4H), 7.17 (d, J=8.5 Hz, 2H), 7.12 (d, J=8.5 Hz, 2H), 7.06 (app, t, J=8.7 Hz, 2H), 5.71 (br dd, J=6.4, 7.9 Hz, 1H), 4.80 (d, J=2.3 Hz, 1H), 4.17-4.13 (m, 1H), 3.85 (dd, J=2.3, 11.6 Hz, 1H), 3.64 (dd, J=6.0, 11.7 Hz, 1H), 3.27-3.22 (m, 2H), 3.18-3.14 (m, 1H), 3.12-3.04 (m, 4H), 2.90-2.85 (m, 1H) 2.92 (s, 3H), 2.75-2.70 (m, 1H), 2.55 (t, 7.7 Hz, 2H), 2.15-2.05 (m, 2H), 2.03 (s, 3H), 1.85-1.80 (m, 4H), 1.75-1.68 (m, 1H).

Step F

N-[3-(4-{(2S,3R)-2-(-(4-{[(2S, 5S, 3R, 4R, 6R)-3,4, 5-trihydroxy-6-(hydroxymethyl)perhydro-2H-pyran-2-yl]ethyl-2-yl}phenyl)-3-[(3S)-3-(4-fluorophenyl)-3-hydroxypropyl]-4-oxoazetidin-1-yl}phenyl)propyl] methanesulfonamide

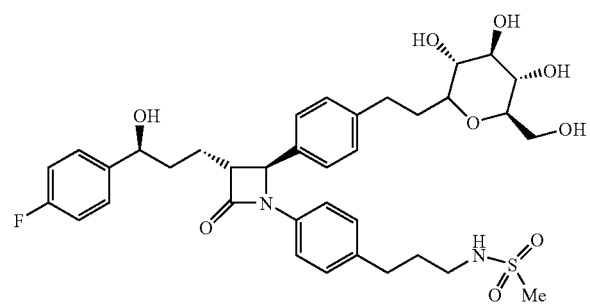

To a solution of the intermediate from Step E, (8 mg, 0.0.12 mmol) in methanol (0.5 mL) was added potassium cyanide (0.5 mg, 0.008 mmol) and the resulting solution stirred at 50° C. for 2 hours. The solution was concentrated and the residue purified by preparative TLC plate eluding with 15% methanol/85% dichloromethane to afford the title compound. m/z (ES) 683 (M-OAc)⁺ and 723 (M+Na)⁺ ¹HNMR (500 MHz, CD₃OD) δ: 7.35-7.31 (m, 2H), 7.28-7.24 (m, 4H), 7.18 (d, J=8.5 Hz, 2H), 7.12 (d, J=8.4 Hz, 2H), 7.03 (app, t, J=8.6 Hz, 2H), 4.79 (br d, J=2.0 Hz, 1H), 4.60 (br dd, J=5.2, 7.0 Hz, 1H), 3.86 (dd, J=2.2, 11.8 Hz, 1H), 3.64 (dd, J=6.0, 11.8 Hz, 1H), 3.27-3.20 (m, 2H), 3.19-3.15 (m, 1H), 3.12-3.03 (m, 4H), 2.91-2.84 (m, 1H), 2.94 (s, 3H), 2.76-2.70 (m, 1H), 2.57 (t, 7.76 Hz, 2H), 2.16-2.06 (m, 1H), 1.97-1.79 (m, 6H), 1.74-1.66 (m, 1H).

EXAMPLE 4

2,6-anhydro-7,8-dideoxy-8-{4-[(2S, 3R)-3-[(3S)-3-(4-fluorophenyl)-3-hydroxypropyl]-1-(4-{3-[methyl(methylsulfonyl)amino]propyl}phenyl)-4-oxoazetidin-2-yl]phenyl}-L-gulo-octonic acid Step A Preparation of 8-{4-[(2S,3R)-3-[(3S)-3-(acetyloxy)-3-(4-fluorophenyl)propyl]-1-(4-{3-[(methylsulfonyl)amino]propyl}phenyl)-4-oxoazetidin-2-yl]phenyl}-2,6-anhydro-7,8-dideoxy-L-gulo-octanoic acid

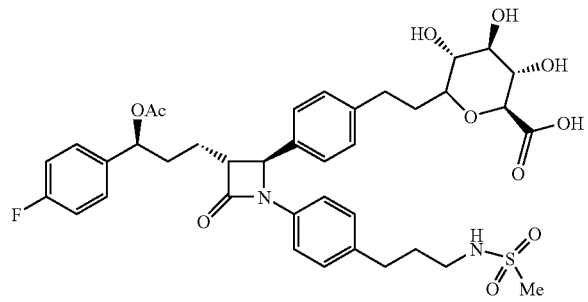

To a solution of the intermediate i-10d wherein R¹⁰ is —H (15 mg, 0.02 mmol) in dichloromethane (1 mL) was added 2,2,6,6 TEMPO free radical (0.1 mg, 0.0004 mmol) followed by a preformed mixture of tetrabutylammonium chloride (0.30 mg, 0.001 mmol) and KBr (0.25 mg, 0.002 mmol) in saturated aqueous solution of sodium bicarbonate (40 μL). The mixture was cooled to 0° C. via ice/water bath and stirred vigorously. A solution of aqueous saturated sodium bicarbonate (20 μL), aqueous saturated sodium chloride (40 μL) and NaOCl (70 μL of a 0.6 M solution) was added dropwise via syringe and the resulting solution stirred for 2 hours allowing to warm to room temperature. The solution was transferred to a separatory funnel and extracted with dichloromethane (3×5 mL). The organics were combined, dried over magnesium sulfate, filtered and concentrated in vacuo. Purification was done by Gilson reverse phase HPLC eluting with a gradient of 25-75% acetonitrile/water (0.1% TFA buffer) over 15 minutes to afford the title compound. m/z (ES) 697 (M-OAc)⁺

Step B 2,6-anhydro-7,8-dideoxy-8-{4-[2S, 3R)-3-[(3S)-3-(4-fluorophenyl)-3-hydroxypropyl]-1-(4-{3-[(methylsulfonyl)amino]propyl}phenyl)-4-oxoazetidin-2-yl]phenyl}-L-gulo-octonic acid

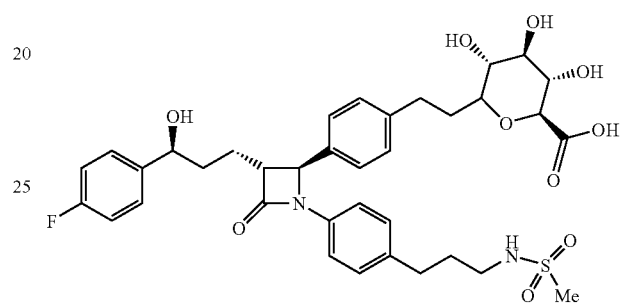

To a solution of the intermediate from Step A (4 mg, 0.005 mmol) in methanol (0.5 mL) was added potassium cyanide (crystal, ~0.1-0.2 mg and the resulting solution stirred at 50° C. for 2 hours. The solution was concentrated in vacuo and the residue purified by Gilson Reverse phase HPLC (gradient eluant 10-75% acetonitrile/water with 0.1% TFA buffer) to afford the title compound. m/z (ES) 697 (M-OH)⁺ and 737 (M+Na)⁺. ¹HNMR (500 MHz, CD₃OD) δ: 7.35-7.31 (m, 2H), 7.28-7.24 (m, 2H), 7.22 (d, J=7.9 Hz, 2H), 7.18 (d, J=8.5 Hz, 2H), 7.13 (d, J=8.5 Hz, 2H), 7.00 (app t, J=8.6 Hz, 2H), 4.79 (d, J=2.3 Hz, 1H), 4.62-4.58 (m, 1H), 3.60 (d, J=10.1 Hz, 1H), 3.50 (t, J=9.5 Hz, 1H), 3.35-3.22 (m, 2H), 3.20-3.13 (m, 2H), 2.90-2.84 (m, 1H) 2.80 (s, 3H), 2.79 (s, 3H), 2.77-2.72 (m, 1H), 2.71-2.66 (m, 1H), 2.58 (t, 7.7 Hz, 2H), 2.16-2.10 (m, 1H), 1.98-1.76 (m, 6H), 1.74-1.68 (m, 1H).

EXAMPLE 5

Preparation of:

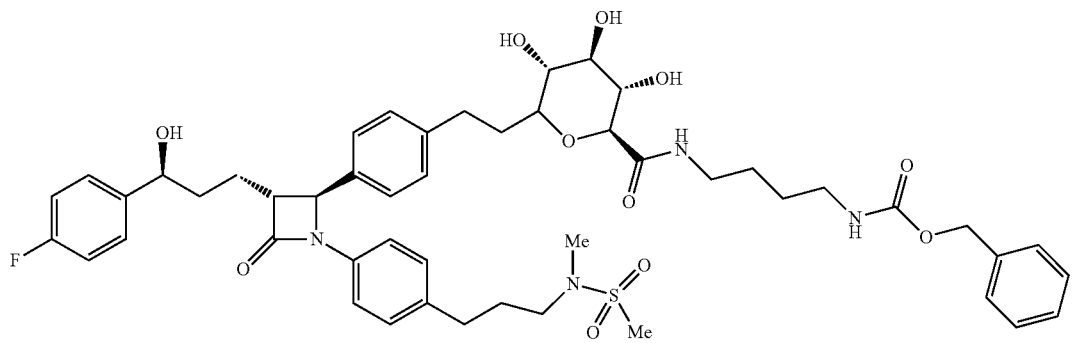

To a solution of N-[3-(4-{(2S,3R)-2-(4-{[(2S, 5S, 3R, 4R, 6S)-3,4,5-trihydroxy-6-(carboxy)perhydro-2H-pyran-2-yl]ethyl-2-yl}phenyl)-3-[(3S)-3-(4-fluorophenyl)-3-hydroxypropyl]-4-oxoazetidin-1-yl}phenyl)propyl]-N-methylmethanesulfonamide (see final product of Example 2) (15 mg, 0.02 mmol) in DMF/DCM (1 mL/1 mL) was added HOBt (3 mg, 0.02 mmol), DIEA (4 µL, 0.02 mmol), benzyl (4-aminobutyl)carbamate (5 mg, 0.02 mmol) and EDC (8 mg, 0.04) and the resulting solution was stirred overnight at room temperature. The solution was concentrated to dryness and the residue purified by preparative plate chromatography (eluting with 10% MeOH/90% dichloromethane) to afford the title compound. m/z (ES) 933 (M+H)+

EXAMPLE 6

Preparation of

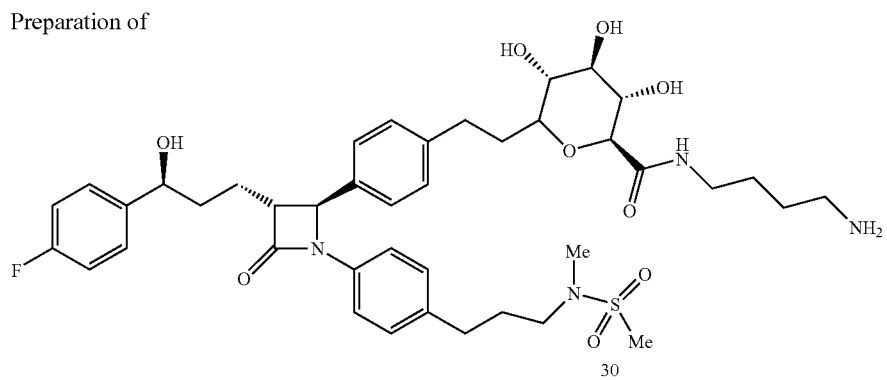

To a solution of the title compound depicted in Example 5 (9.3 mg, 0.01 mmol) in ethyl acetate 1 mL) and 2N HCl in ether (5 µL) was added 10% palladium on activated carbon (10 mg) and the resulting suspension was set under hydrogen atmosphere and stirred vigorously for 2 hours. The catalyst was filtered off using a Gilmen 0.45 µM PTFE syringe filter and washed with ethyl acetate (2×5 mL). The organics were combined, concentrated to dryness in vacuo and the residue purified by Gilson reverse phase HPLC (gradient elution: 10-75% acetonitrile in water, 0.1% TFA buffer) to afford the title compound. m/z (ES) 799 (M+H)+. $^1$HNMR (500 MHz, CD$_3$OD) δ: 8.04 (m, 1H), 7.35-7.30 (m, 2H), 7.28 (d, J=8.1 Hz, 2H), 7.23 (d, J=8.0 Hz, 2H), 7.18 (d, J=8.2 Hz, 2H), 7.12 (d, J=8.4 Hz, 2H), 7.03 (app t, J=8.6 Hz, 2H), 4.81 (d, J=2.4 Hz, 1H), 4.61 (br dd, J=5.2, 7.0 Hz, 1H), 3.60 (d, J=9.6 Hz, 2H), 3.44 (t, J=9.5 Hz, 2H), 3.20-3.08 (m, 6H), 3.06-3.02 (m, 1H), 2.98-2.93 (m, 2H), 2.90-2.80 (m, 1H), 2.80 (s, 3H), 2.79 (s, 3H), 2.72-2.65 (m, 1H), 2.58 (t, J=7.6 Hz, 2H), 2.21-2.14 (m, 1H), 2.00-1.80 (m, 7H) 1.72-1.61 (m, 4H).

EXAMPLE 7

Employing procedures similar to those described in Examples 1-6, the following compounds in Table 1 can be prepared:

7A

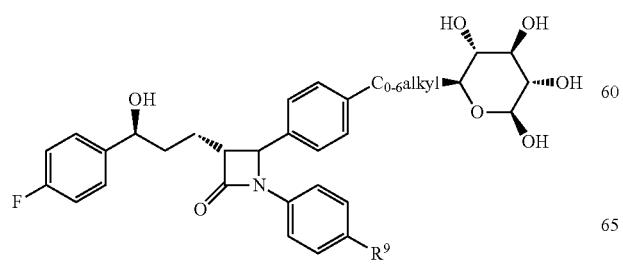

-continued

7B

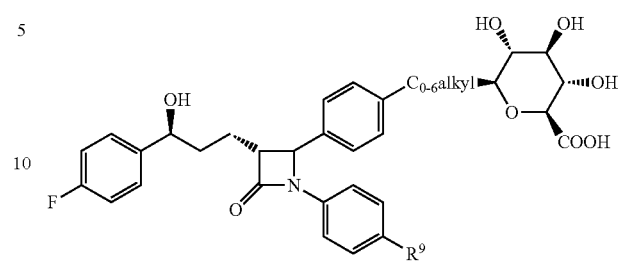

In this Example, y is an integer selected from 2, 3, 4, 5 and 6.

TABLE 1

| Ex. #7A | Ex. #7B | $R^9$ |
|---|---|---|
| a) | a) | ⤳NH$_2$ |
| b) | b) | ⤳NHC(O)Me |
| c) | c) | ⤳N(Me)S(O)$_2$Me |
| d) | d) | ⤳NHS(O)$_2$Ph |
| e) | e) | ⤳NHS(O)$_2$Ph |
| f) | f) | ⤳N(Me)S(O)$_2$Ph |

TABLE 1-continued

| Ex. #7A | Ex. #7B | R⁹ |
|---|---|---|
| g) | g) | (structure: alkyl-NH-C(=O)-N(Me)Me) |
| h) | h) | (structure: alkyl-N(Me)-C(=O)-N(Me)Me) |
| i) | i) | (structure: alkyl-NH-Me) |
| j) | j) | (structure: alkyl-N(Me)Me) |
| k) | k) | (structure: (alkyl)y-NH₂) |
| l) | l) | (structure: (alkyl)y-NH-C(=O)-Me) |
| m) | m) | (structure: (alkyl)y-NH-S(O₂)-Me) |
| n) | n) | (structure: alkyl-N(Me)-S(O₂)-Me) |
| o) | o) | (structure: (alkyl)y-NH-S(O₂)-Ph) |
| p) | p) | (structure: (alkyl)y-N(Me)-S(O₂)-Ph) |
| q) | q) | (structure: (alkyl)y-NH-C(=O)-N(Me)Me) |
| r) | r) | (structure: (alkyl)y-N(Me)-C(=O)-N(Me)Me) |
| s) | s) | (structure: (alkyl)y-NH-Me) |
| t) | t) | (structure: (alkyl)y-N(Me)Me) |

While the invention has been described and illustrated with reference to certain particular embodiments thereof, those skilled in the art will appreciate that various changes, modifications and substitutions can be made therein without departing from the spirit and scope of the invention. For example, effective dosages other than the particular dosages as set forth herein above may be applicable as a consequence of variations in the responsiveness of the mammal being treated for any of the indications for the active agents used in the instant invention as indicated above. Likewise, the specific pharmacological responses observed may vary according to and depending upon the particular active compound selected or whether there are present pharmaceutical carriers, as well as the type of formulation employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of structural Formula I

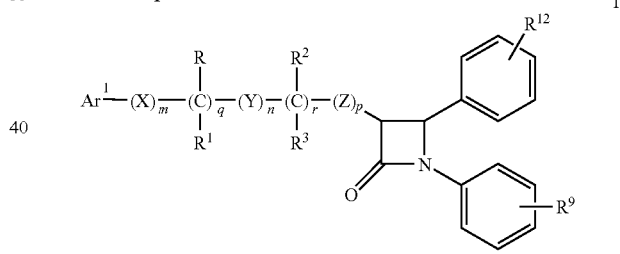

and the pharmaceutically acceptable salts and esters thereof, wherein $Ar^1$ is selected from the group consisting of aryl and $R^4$-substituted aryl;

X, Y and Z are independently selected from the group consisting of —CH$_2$—, —CH(C$_{1-6}$alkyl)— and —C(C$_{1-6}$alkyl)$_2$—;

R is selected from the group consisting of —OR$^6$, —O(CO)R$^6$, —O(CO)OR$^8$, —O(CO)NR$^6$R$^7$, a sugar residue, a disugar residue, a trisugar residue and a tetrasugar residue;

$R^1$ is selected from the group consisting of —H, —C$_{1-6}$ alkyl and aryl, or R and $R^1$ together are oxo;

$R^2$ is selected from the group consisting of —OR$^6$, —O(CO)R$^6$, —O(CO)OR$^8$ and —O(CO)NR$^6$R$^7$;

$R^3$ is selected from the group consisting of —H, —C$_{1-6}$ alkyl and aryl or $R^2$ and $R^3$ together are oxo;

q and r are integers each independently selected from 0 and 1 provided that at least one of q and r is 1;

m, n and p are integers each independently selected from 0, 1, 2, 3 and 4, provided that the sum of m, n, p, q and r is 1, 2, 3, 4, 5 or 6;

t is an integer selected from 0, 1 and 2;

$R^4$ is 1-5 substituents independently selected at each occurrence from the group consisting of:
—$OR^5$, —$O(CO)R^5$, —$O(CO)OR^8$, —O—$C_{1-5}$alkyl-$OR^5$, —$O(CO)NR^5R^6$, —$NR^5R^6$, —$NR^5(CO)R^6$, —$NR^5(CO)OR^8$, —$NR^5(CO)NR^6R^7$, —$NR^5SO_2R^8$, —$COOR^5$, —$CONR^5R^6$, —$COR^5$, —$SO_2NR^5R^6$, —$S(O)_tR^8$, —O—$C_{1-10}$alkyl-$COOR^5$, —O—$C_{1-10}$alkyl-$CONR^5R^6$ and fluoro;

$R^5$, $R^6$ and $R^7$ are independently selected at each occurrence from the group consisting of —H, —$C_{1-6}$alkyl, aryl and aryl-substituted —$C_{1-6}$alkyl;

$R^8$ is independently selected from the group consisting of —$C_{1-6}$alkyl, aryl and aryl-substituted —$C_{1-6}$alkyl;

$R^9$ is selected from the group consisting of —C≡C—$(CH_2)_y$—$NR^{10}R^{11}$, —$(CH_2)_2$—$(CH_2)_y NR^{10}R^{11}$ and —C≡C—$C(O)R^{16}$;

$R^{10}$ is independently selected at each occurrence from —H and —$C_{1-3}$alkyl;

$R^{11}$ is selected from the group consisting of —H, —$C_{1-3}$alkyl, —C(O)—$C_{1-3}$alkyl, —C(O)—$NR^{10}R^{10}$, —$SO_2$—$C_{1-3}$alkyl, and —$SO_2$-phenyl; and $R^{12}$ is selected from the group consisting of $R^{13}$, —$C_{1-8}$alkyl-$R^{13}$, —CH═CH—$(CH_2)_w$—$R^{13}$ and —C≡C—$(CH_2)_w$—$R^{13}$, provided that when $R^{12}$ is —$C_{1-8}$alkyl-$R^{13}$ then $R^9$ is —$(CH_2)_2$—$(CH_2)_y NR^{10}R^{11}$;

w is an integer independently selected at each occurrence from 0, 1, 2, 3, 4, 5 and 6;

y is an integer independently selected at each occurrence from 1, 2, 3, 4, 5 and 6;

$R^{13}$ is

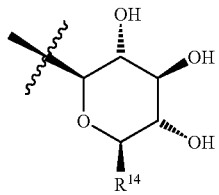

$R^{14}$ is selected from the group consisting of —COOH, —$COOC_{1-6}$alkyl, —$CH_2OH$, —$CH_2O(CH_2)_y$—$R^{15}$, —$CONR^{10}R^{10}$ and

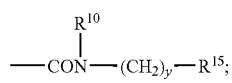

$R^{15}$ is independently selected at each occurrence from the group consisting of —H, —OH, —$COOR^{10}$, —$NR^{10}R^{17}$, —$NR^{10}COR^{17}$, —$NR^{10}COOR^{17}$, —$NR^{10}$—$SO_2R^{17}$ and —$NR^{10}$—$CONR^{10}R^{17}$;

$R^{16}$ is selected from the group consisting of —OH, —$OC_{1-6}$ alkyl and —$NR^{10}R^{11}$; and $R^{17}$ is selected from the group consisting of —H, —$C_{1-3}$alkyl, phenyl and —$CH_2$-phenyl.

2. The compound of claim 1 having structural Formula Ia

Ia

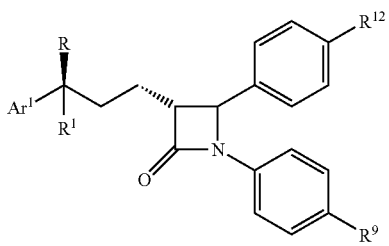

and the pharmaceutically acceptably salts and esters thereof.

3. The compound of claim 2 having structural Formula Ib

Ib

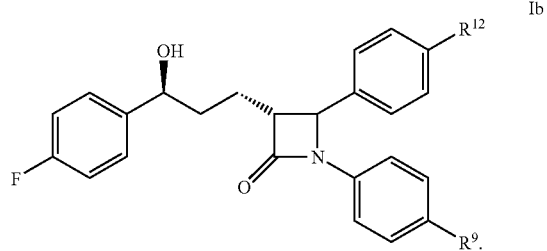

4. The compound of claim 1 wherein $R^9$ is selected from —C≡C—$(CH_2)_y$—$NR^{10}R^{11}$ and —$(CH_2)_2$—$(CH_2)_y NR^{10}R^{11}$.

5. The compound of claim 4 wherein $R^9$ is selected from —C≡C—$CH_2$—$NR^{10}R^{11}$ and —$(CH_2)_3$—$NR^{10}R^{11}$.

6. The compound of claim 5 wherein $R^9$ is selected from —C≡C—$CH_2$—$N(R^{10})(SO_2$—$C_{1-3}$alkyl), —C≡C—$CH_2$—$N(R^{10})(SO_2$-phenyl), —$(CH_2)_3$—$N(R^{10})(SO_2$—$C_{1-3}$alkyl) and —$(CH_2)_3$—$N(R^{10})(SO_2$-phenyl).

7. The compound of claim 1 wherein $R^{12}$ is selected from $R^{13}$, —$CH_2$—$R^{13}$, —$CH_2$—$CH_2$—$R^{13}$ and —C≡C—$R^{13}$.

8. The compound of claim 4 wherein $R^{12}$ is selected from $R^{13}$, —$CH_2$—$R^{13}$, —$CH_2$—$CH_2$—$R^{13}$ and —C≡C—$R^{13}$.

9. The compound of claim 5 wherein $R^{12}$ is selected from $R^{13}$, —$CH_2$—$R^{13}$, —$CH_2$—$CH_2$—$R^{13}$ and —C≡C—$R^{13}$.

10. The compound of claim 6 wherein $R^{12}$ is selected from $R^{13}$, —$CH_2$—$R^{13}$, —$CH_2$—$CH_2$—$R^{13}$ and —C≡C—$R^{13}$.

11. The compound of claim 8 wherein $Ar^1$ is selected from the group consisting of aryl and $R^4$-substituted aryl wherein $R^4$ is 1-2 substituents independently selected at each occurrence from the group consisting of: —$OR^5$, —$O(CO)R^5$, —$O(CO)OR^8$, —O—$C_{1-5}$-alkyl-$OR^5$, —$O(CO)NR^5R^6$, —$NR^5R^6$, —$NR^5(CO)R^6$, —$NR^5(CO)OR^8$, —$NR^5(CO)NR^6R^7$, —$NR^5SO_2R^8$, —$COOR^5$, —$CONR^5R^6$, —$COR^5$, —$SO_2NR^5R^6$, —$S(O)_tR^8$, —O—$C_{1-10}$alkyl-$COOR^5$, —O—$C_{1-10}$alkyl-$CONR^5R^6$ and fluoro.

12. The compound of claim 11 wherein R is —$OR^6$ and $R^1$ is —H.

13. The compound of claim 1 selected from:

N-[3-(4-{(2S,3R)-2-(-(4-{[(2S, 5S, 3R, 4R, 6R)-3,4,5-trihydroxy-6-(hydroxymethyl)perhydro-2H-pyran-2-yl]ethyl-2-yl}phenyl)-3-[(3S)-3-(4-fluorophenyl)-3-hydroxypropyl]-4-oxoazetidin-1-yl}phenyl)propyl]-N-methylmethanesulfonamide;

N-[3-(4-{(2S,3R)-2-(4-{[(2S, 5S, 3R, 4R, 6S)-3,4,5-trihydroxy-6-(carboxy)perhydro-2H-pyran-2-yl]ethyl-2-yl}phenyl)-3-[(3S)-3-(4-fluorophenyl)-3-hydroxypropyl]-4-oxoazetidin-1-yl}phenyl)propyl]-N-methylmethanesulfonamide;

N-[3-(4-{(2S,3R)-2-(-(4-{[2S, 5S, 3R, 4R, 6R)-3,4,5-trihydroxy-6-(hydroxymethyl)perhydro-2H-pyran-2-yl]ethyl-2-yl}phenyl)-3-[(3S)-3-(4-fluorophenyl)-3-hydroxypropyl]-4-oxoazetidin-1-yl}phenyl)propyl]methanesulfonamide;

2,6-anhydro-7,8-dideoxy-8-{4-[(2S, 3R)-3-[(3S)-3-(4-fluorophenyl)-3-hydroxypropyl]-1-(4-{3-[methyl(methylsulfonyl)amino]propyl}phenyl)-4-oxoazetidin-2-yl]phenyl}-L-gulo-octonic acid;

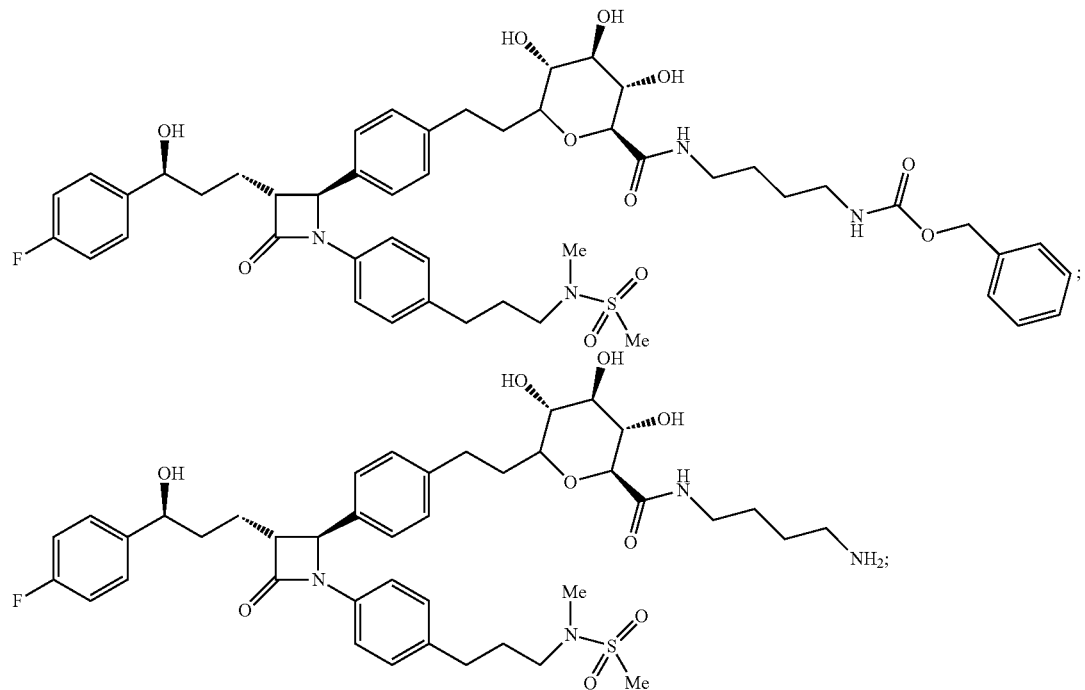

and the pharmaceutically acceptable salts and esters thereof.

14. A method of reducing plasma LDL-cholesterol levels comprising administering a therapeutically effective amount of a compound of claim 1 to a patient in need of such treatment.

15. The method of claim 14 comprising administering a therapeutically effective amount of a compound of claim 1 in combination with a therapeutically effective amount of a cholesterol biosynthesis inhibitor to a patient in need of such treatment.

16. A method of treating hypercholesterolemia comprising administering a therapeutically effective amount of a compound of claim 1 to a patient in need of such treatment.

17. A method of treating atherosclerosis comprising administering a therapeutically effective amount of a compound of claim 1 to a patient in need of such treatment.

18. A pharmaceutical composition comprising a compound of claim 1 and a pharmaceutically acceptable carrier.

19. The pharmaceutical composition of claim 15 additionally comprising a cholesterol biosynthesis inhibitor.

* * * * *